(12) United States Patent
Leimbach et al.

(10) Patent No.: US 10,704,624 B2
(45) Date of Patent: Jul. 7, 2020

(54) DRIVE CABLE BRAKE ASSEMBLY FOR ROBOTIC SURGICAL TOOL

(71) Applicant: Ethicon LLC, Guaynabo, PR (US)

(72) Inventors: Richard L. Leimbach, Cincinnati, OH (US); Mark Zeiner, Mason, OH (US); Gregory Bakos, Mason, OH (US); Daniel Mumaw, Liberty Township, OH (US); Thomas Tate, Cincinnati, OH (US); Joshua Young, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 367 days.

(21) Appl. No.: 15/794,449

(22) Filed: Oct. 26, 2017

(65) Prior Publication Data

US 2019/0128347 A1 May 2, 2019

(51) Int. Cl.
| | | |
|---|---|---|
| A61B 17/22 | (2006.01) | |
| F16D 63/00 | (2006.01) | |
| A61B 34/00 | (2016.01) | |
| A61B 34/30 | (2016.01) | |
| A61B 17/00 | (2006.01) | |

(52) U.S. Cl.
CPC ...... *F16D 63/008* (2013.01); *A61B 17/00234* (2013.01); *A61B 34/30* (2016.02); *A61B 34/71* (2016.02); *A61B 2017/00323* (2013.01); *A61B 2017/00477* (2013.01); *A61B 2034/302* (2016.02)

(58) Field of Classification Search
CPC ....... F16D 63/008; A61B 34/30; A61B 17/00; A61B 17/56; A61B 19/00
USPC ............. 188/68, 74; 606/103, 159, 205, 206
See application file for complete search history.

(56) References Cited

U.S. PATENT DOCUMENTS

| | | | | |
|---|---|---|---|---|
| 5,314,407 A | * | 5/1994 | Auth | ................ A61B 17/32075 604/22 |
| 8,831,782 B2 | | 9/2014 | Itkowitz | |

(Continued)

FOREIGN PATENT DOCUMENTS

| | | |
|---|---|---|
| EP | 0654245 A1 | 5/1995 |
| EP | 2712538 A1 | 4/2014 |

(Continued)

OTHER PUBLICATIONS

ISRWO for corresponding PCT/IB2018/058081 dated Feb. 4, 2019.

*Primary Examiner* — Christopher P Schwartz
(74) *Attorney, Agent, or Firm* — Vorys, Sater, Seymour and Pease LLP

(57) ABSTRACT

A surgical tool that includes a drive housing, an elongate shaft that extends from the drive housing, and a plurality of drive cables extending within the elongate shaft between the drive housing and an end effector coupled to a distal end of the elongate shaft. A cable brake assembly is at least partially arranged within a cavity defined in the drive housing or the elongate shaft, the cable brake assembly having one or more brakes and a brake pad engageable with one or more of the plurality of drive cables. The cable brake assembly is actuatable between a first position, where the plurality of drive cables are free to move longitudinally within the elongate shaft, and a second position, where the one or more brakes and the brake pad engage and prevent the one or more of the plurality of drive cables from moving.

20 Claims, 11 Drawing Sheets

(56) References Cited

U.S. PATENT DOCUMENTS

2004/0199052 A1   10/2004   Banik et al.
2015/0313676 A1   11/2015   Deodhar
2016/0287252 A1   10/2016   Parihar

FOREIGN PATENT DOCUMENTS

WO   2014/151621   9/2014
WO   2014/151952   9/2014

* cited by examiner

US 10,704,624 B2

DRIVE CABLE BRAKE ASSEMBLY FOR ROBOTIC SURGICAL TOOL

BACKGROUND

Minimally invasive surgical (MIS) instruments are often preferred over traditional open surgical devices due to reduced post-operative recovery time and minimal scarring. Endoscopic surgery is one type of MIS procedure in which an elongate flexible shaft is introduced into the body of a patient through a natural orifice. Laparoscopic surgery is another type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity, and the trocar also helps facilitate insufflation to elevate the abdominal wall above the organs. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint on the instrument, which creates a more natural hand-like articulation.

To facilitate the wrist joint, robotic systems typically include a cable driven motion system designed to articulate (move) an end effector of a surgical instrument. Cable driven motion systems typically include one or more drive cables that extend between a drive housing and the end effector. The drive housing is mounted to and otherwise attached to a robotic manipulator that has a plurality of input drives operatively coupled to the drive cables. During operation, the input drives are selectively actuated to move the drive cables and thereby articulate the end effector in a desired manner.

Through operation of the input drives, the drive cables typically assume large tensile loads, which must be released or eased prior to detaching the drive housing from the robotic manipulator. If such tensile loads are not previously released, detaching the drive housing from the robotic manipulator can suddenly release the tension in the drive cables, which, in extreme cases, could launch the drive housing from the robotic manipulator and potentially damage the drive housing or harm a user. What is needed is a manual method, independent of the robotically controlled systems to manage cable tension, to provide a safe alternative to disconnecting the drive housing from the robotic manipulator by a user (e.g., surgeon, clinician, etc.) during emergency conditions or when the robotic system is not functioning properly.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgery systems and, more particularly, to methods and systems of inhibiting unintended drive cable translation in highly articulated surgical tools used in robotic surgery.

The embodiments disclosed herein describe mechanisms (sometimes referred to as anti-reverse mechanisms or cable brake assemblies) that inhibit axial translation of one or more drive cables within a surgical tool and thus help prevent unintended articulation of the tool's end effector, for example, during removal of the tool from the robotic assembly. The mechanism includes brakes and an opposing brake pad designed to be selectively engaged by a user, whereby the cables are prevented from translating proximally and/or distally when the brakes and brake pad are engaged. This mechanism helps prevent unintended end effector articulation, for example, in bail out or other emergency situations where a user manually overrides a robotic surgical system to remove the surgical tool. The mechanism also includes various embodiments wherein rotation of the mechanism (i.e., pivoting motion or pitch movement) is inhibited. The mechanism also includes embodiments where it may be selectively locked in an engaged or "braking" position.

Figure 1:
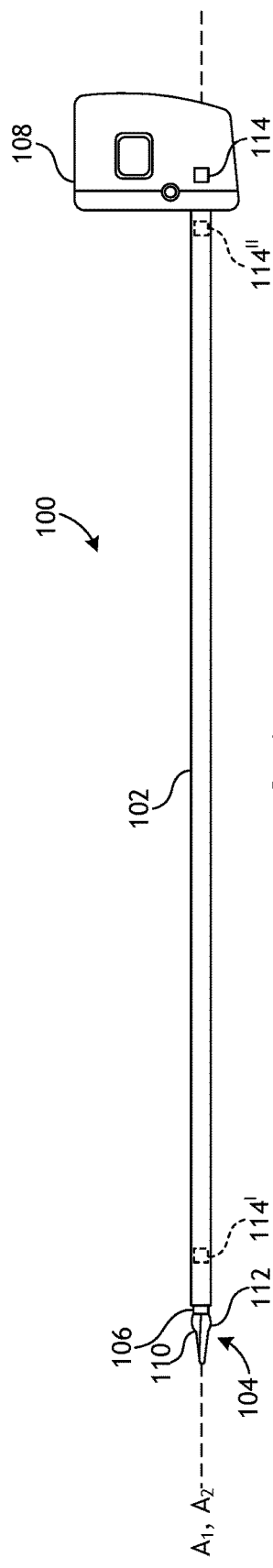
FIG. 1 is a side view of an example surgical tool that may incorporate some or all of the principles of the present disclosure.

FIG. 1 is side view of an example surgical tool 100 that may incorporate some or all of the principles of the present disclosure. As illustrated, the surgical tool 100 includes an elongate shaft 102, an end effector 104 arranged at a distal end of the shaft 102, a wrist 106 that couples the end effector 104 to the shaft 102, and a drive housing 108 coupled to a proximal end of the shaft 102. In at least some embodiments, the surgical tool 100 may be designed to be releasably coupled to a robotic surgical system (not illustrated), and the drive housing 108 can include coupling features that releasably couple the surgical tool 100 to the robotic surgical system.

The terms "proximal" and "distal" are defined herein relative to a robotic surgical system having an interface configured to mechanically and electrically couple the surgical tool 100 to a robotic manipulator of a robotic surgical system. The term "proximal" refers to the position of an element closer to the robotic manipulator and the term "distal" refers to the position of an element closer to the end effector 104 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 100, the end effector 104 is configured to move (pivot) relative to the shaft 102 at the wrist 106 to position the end effector 104 at a desired orientation and location relative to a surgical site. The drive housing 108 includes various mechanisms designed to control operation of various features associated with the end effector 104 (e.g., clamping, firing, rotation, articulation, energy delivery, etc.). In at least some embodiments, the shaft 102, and hence the end effector 104 coupled thereto, is configured to rotate about a longitudinal axis $A_1$ of the shaft 102. In such embodiments, the various mechanisms included in the drive housing 108 are configured to control the rotational movement of the shaft 102.

The shaft 102 is an elongate member extending distally from the drive housing 108 and has at least one lumen extending therethrough along its axial length. The shaft 102 may be fixed to the drive housing 108, but could alternatively be releasably coupled to the drive housing 108 to allow the shaft 102 to be interchangeable with other shafts. Consequently, this may allow a single drive housing 108 to be adaptable to various shafts having different end effectors.

The end effector 104 can have a variety of sizes, shapes, and configurations. In the illustrated embodiment, the end effector 104 comprises a tissue grasper having opposing jaws 110, 112 configured to move between open and closed positions. One or both of the jaws 110, 112 may be configured to pivot at the wrist 106 between open and closed positions. In other embodiments, however, the end effector 104 may have other configurations such as, but not limited to, scissors having opposed cutting blades, forceps (e.g., a babcock) having opposed grasping jaws, a retractor, a hook, a spatula, a needle driver, a stapler, a clip applier, a suction tool, an irrigation tool, an imaging device (e.g., an endoscope or ultrasonic probe), or any combination thereof. In at least one embodiment, the end effector 104 may also comprise an electro cautery tool (energized monopolar or bipolar energy) configured to transmits electrical energy to tissue in the form of heat to cut, cauterize, and/or coagulate tissue.

The wrist 106 can have any of a variety of configurations. Example embodiments and configurations of the wrist 106 are described in U.S. Patent Pub. No. 2015/0209965 entitled "Compact Robotic Wrist," and U.S. Patent Pub. No. 2015/0025549 entitled "Hyperdexterous Surgical System," the contents of which are hereby incorporated by reference in their entirety. The wrist 106 generally comprises a joint configured to allow pivoting movement of the end effector 104 relative to the shaft 102, such as a pivot joint at which the jaws 110, 112 are pivotally attached.

Figure 2:
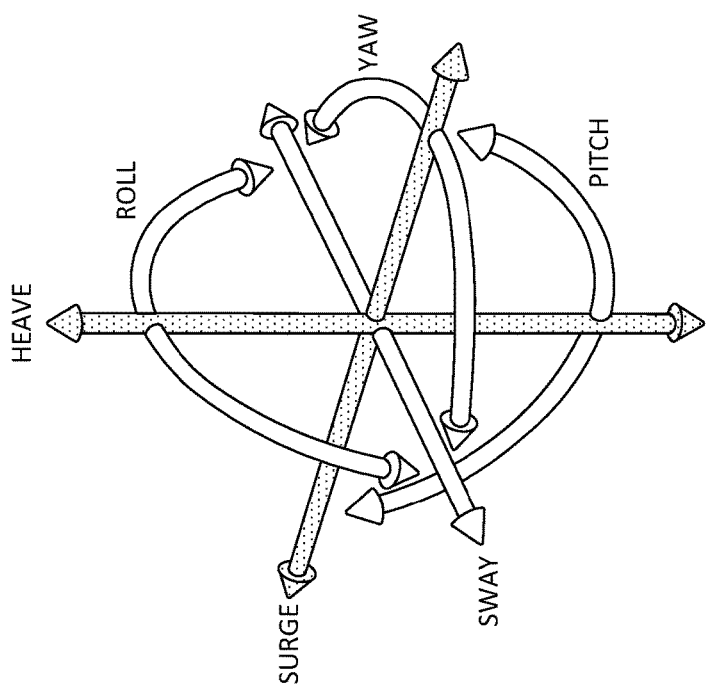
FIG. 2 illustrates potential degrees of freedom in which the wrist of FIG. 1 may be able to articulate (pivot).

FIG. 2 illustrates the potential degrees of freedom in which the wrist 106 may be able to articulate (pivot). The degrees of freedom of the wrist 106 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 104) with respect to a given reference Cartesian frame. As depicted in FIG. 2, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 106 (e.g., X-axis), yaw movement about a second axis of the wrist 106 (e.g., Y-axis), and combinations thereof to allow for 360° rotational movement of the end effector 104 about the wrist 106. In other applications, the pivoting motion can be limited to movement in a single plane, e.g., only pitch movement about the first axis of the wrist 106 or only yaw movement about the second axis of the wrist 106, such that the end effector 104 moves only in a single plane.

Referring again to FIG. 1, the surgical tool 100 includes a plurality of drive cables (obscured in FIG. 1) that form part of a cable driven motion system configured to effect movement (pivoting) of the end effector 104 relative to the shaft 102. The drive cables may be referred to and otherwise characterized as cables, bands, lines, cords, wires, ropes, strings, twisted strings, elongate members, etc. The drive cables can be made from a variety of materials including, but not limited to, metal (e.g., tungsten, stainless steel, etc.), a polymer (e.g., VECTRAN™), or a composite material. In some embodiments, the drive cables may be made of any of the aforementioned materials (or any combination thereof) and may be shrouded in a metal housing. Example drive cables are described in previously mentioned U.S. Patent Pub. Nos. 2015/0209965 and 2015/0025549.

The drive cables are operably coupled to various actuation mechanisms housed within the drive housing 108 and extend within the lumen of the shaft 102 to the wrist 106 where they are operably engaged with the end effector 104. Selective actuation of the drive cables causes the end effector 104 (e.g., one or both of the jaws 110, 112) to move (pivot) relative to the shaft 102. More specifically, selective actuation of the drive cables can cause any one or more of the drive cables to translate longitudinally within the lumen of the shaft 102 and thereby cause movement of the end effector 104. For example, one or more drive cables may translate longitudinally to cause the end effector 104 to articulate (e.g., both of the jaws 110, 112 angle in a same direction), to cause the end effector 104 to open (e.g., one or both of the jaws 110, 112 move away from the other), or to cause the end effector 104 to close (e.g., one or both of the jaws 110, 112 move toward the other).

Actuation of the drive cables can be accomplished in a variety of ways, such as by triggering an associated actuator operably coupled to or housed within the drive housing 108. For example, actuation may apply tension to (i.e., pulls) the drive cables in a proximal direction to cause the corresponding elongate member to translate and thereby cause the end effector 104 to move (articulate) relative to the shaft 102. When both of the jaws 110, 112 are designed to move to open and close the end effector 104, one or more first drive cables will be operably coupled to the first jaw 110 to move that jaw 110 and one or more second drive cables will be operably coupled to the second jaw 112 to move that jaw 112. When only one of the jaws 110, 112 is configured to move to open and close the end effector 104, one or more drive cables may be operably coupled to the first jaw 110 to move the first jaw 110 relative to the second jaw 112.

Actuating the drive cables moves the end effector 104 between an unarticulated position and an articulated position. The end effector 104 is depicted in FIG. 1 in the unarticulated position where a longitudinal axis $A_2$ of the end effector 104 is substantially aligned with the longitudinal axis $A_1$ of the shaft 102, such that the end effector 104 is at a substantially zero angle relative to the shaft 102. Due to factors such as manufacturing tolerance and precision of measurement devices, the end effector 104 may not be at a precise zero angle relative to the shaft 102 in the unarticulated position, but nevertheless be considered "substantially aligned" thereto. In the articulated position, the longitudinal axes $A_1$, $A_2$ would be angularly offset from each other such that the end effector 104 is at a non-zero angle relative to the shaft 102.

The drive housing 108 (alternately referred to as a "puck") may be releasably latched (attached) to a tool driver of a robotic surgical system in a variety of ways, such as by clamping thereto, clipping thereto, or slidably mating therewith. The drive housing may have a plurality of input drives, each corresponding to one or more of the drive cables and each interfacing with a corresponding output drive of the tool driver of the robotic surgical system. The input drives may be controlled by the robot based on user inputs received via a computer system incorporated into the robot. Accordingly, the user inputs control movement of the drive cables and consequently movement of the end effector 104.

The drive housing 108 illustrated in FIG. 1 is but one example of a suitable drive housing, and additional embodiments of the drive housing 108 are described in previously mentioned U.S. Patent Pub. Nos. 2015/0209965 and 2015/0025549. Example robotic surgical systems are described in U.S. Pat. No. 8,831,782 entitled "Patient-Side Surgeon Interface for a Teleoperated Surgical Instrument," the contents of which are hereby incorporated by reference, and previously mentioned U.S. Patent Pub. Nos. 2015/0209965 and 2015/0025549.

Figure 3:
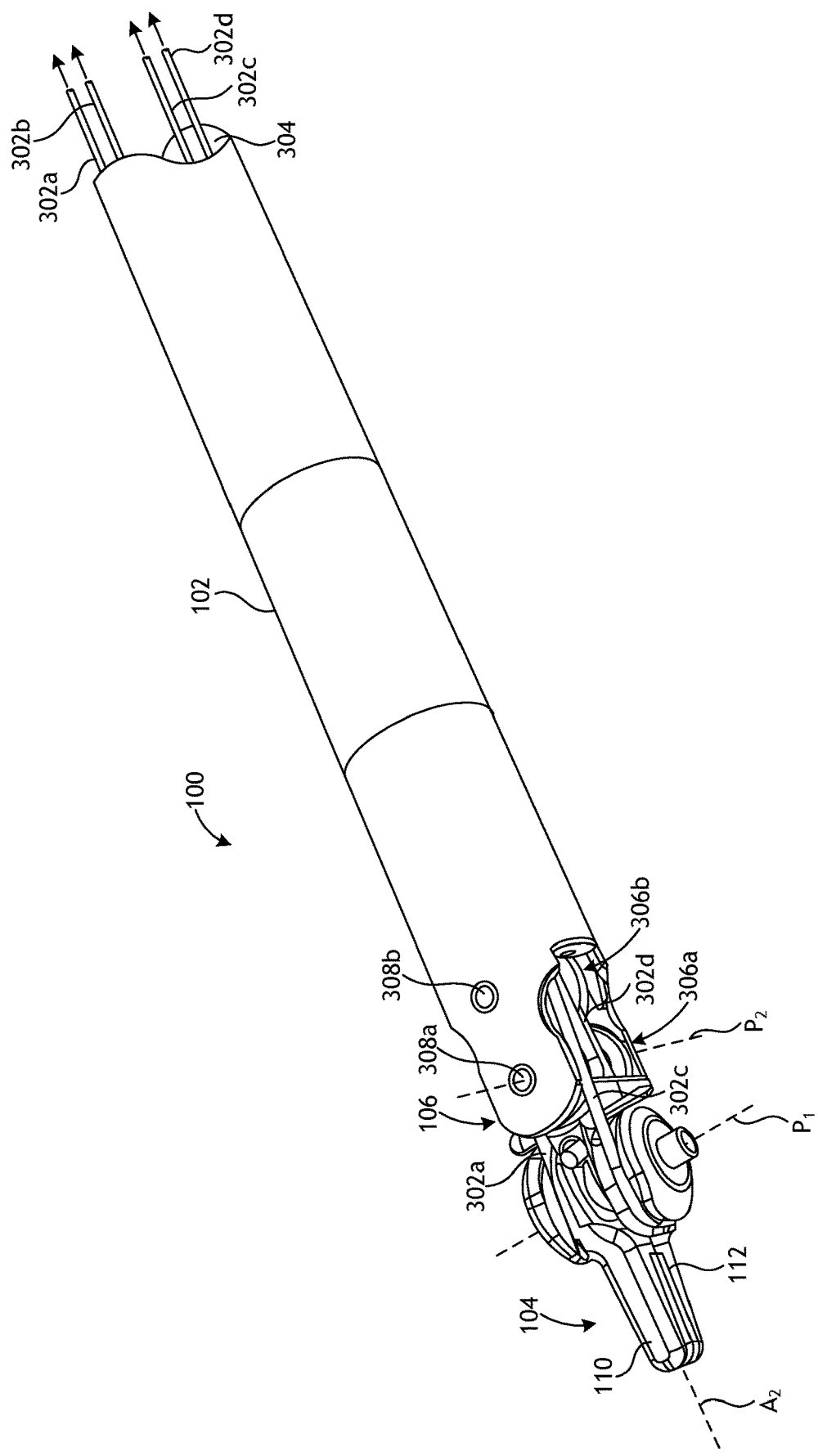
FIG. 3 is an enlarged isometric view of the distal end of the surgical tool of FIG. 1.

FIG. 3 is an enlarged isometric view of the distal end of the surgical tool 100 of FIG. 1. More specifically, FIG. 3 depicts enlarged views of the end effector 104 and the wrist 106, with the end effector 104 in the unarticulated position where the jaws 110, 112 are closed. A plurality of drive cables 302, shown as drive cables 302a, 302b, 302c, and 302d, extend longitudinally within a lumen 304 of the shaft 102 until terminating at the wrist 106. The drive cables 302a-d extend proximally from the end effector 104 to the drive housing 108 (FIG. 1) which, as discussed above, may be configured to facilitate longitudinal movement of the drive cables 302a-d within the lumen 304. The lumen 304 can be a single lumen, as illustrated, or can alternatively comprise a plurality of independent lumens that each receive one of the drive cables 302a-d.

The wrist 106 includes a first plurality of pulleys 306a and a second plurality of pulleys 306b each configured to interact with and redirect the drive cables 308a-d for engagement with the end effector 104. The first plurality of pulleys 306a is mounted to a first wrist axle 308a and the second plurality of pulleys 306b is mounted to a second wrist axle 308b. The first and second pluralities of pulleys 306a,b cooperatively redirect the drive cables 302a-d through an "S" shaped pathway.

In at least one embodiment, one pair of drive cables 302a-d is operatively coupled to each other at the jaws 110, 112 and configured to "antagonistically" operate the corresponding jaw 110, 112. In the illustrated embodiment, for example, the first and second drive cables 308a,b are operatively coupled to the first jaw 110, and the third and fourth drive cables 308c,d are operatively coupled to the second jaw 112. Actuation of the first drive cable 308a pivots the first jaw 110 about a first pivot axis $P_1$ toward the open position, where the first pivot axis $P_1$ is substantially perpendicular to the longitudinal axis $A_2$ of the end effector 104. In contrast, actuation of the second drive cable 308b pivots the first jaw 110 about the first pivot axis $P_1$ in the opposite direction and toward the closed position. Similarly, actuation of the third drive cable 308c pivots the second jaw 112 about the first pivot axis $P_1$ toward the open position, while actuation of the fourth drive cable 308d pivots the second jaw 112 about the first pivot axis $P_1$ in the opposite direction and toward the closed position.

Accordingly, actuation of the drive cables 302a-d causes relative or tandem movement of the first and second jaws 110, 112 at their respective joints. The drive cables 308a-d may thus be characterized or otherwise referred to as "antagonistic" cables that cooperatively (antagonistically) operate to cause relative or tandem movement of the first and second jaws 110, 112. When the first drive cable 302a is actuated, the second drive cable 302b naturally follows as operatively coupled to the first drive cable 302b at the first jaw 110, and vice versa. Similarly, when the third drive cable 302c is actuated, the fourth drive cable 302d naturally follows as operatively coupled to the third drive cable 308c at the second jaw 112, and vice versa.

The surgical tool 100 may also have a second pivot axis $P_2$ extending through the first wrist axle 308a and about which the end effector 104 is configured to articulate relative to the shaft 102. More particularly, actuation of one or more of the drive cables 302a-d causes movement of the wrist 106 at the second pivot axis $P_2$, and hence articulation of the end effector 104. Consequently, the end effector 104 can articulate with multiple degrees of freedom, e.g., a degree of freedom by articulating about the first pivot axis $P_1$ and another degree of freedom by articulating about the second pivot axis $P_2$. The wrist 106 in this embodiment is pivotable about the second pivot axis $P_2$ in a single plane, e.g., in one of pitch and yaw, and the end effector 104 is pivotable about the first pivot axis $P_1$ in a single, different plane, e.g., the other of pitch and yaw.

Referring again to FIG. 1, according to the present disclosure, the surgical tool 100 may further include a cable brake assembly 114 configured to be selectively actuated to bind the drive cables 302a-d (FIG. 3) and thereby prevent unintentional movement (translation) thereof. Unintentional movement of the drive cables 302a-d may occur, for example, upon detaching the drive housing 108 from a robotic manipulator of a robotic surgical system used to operate the surgical tool 100. Since the drive cables 302a-d operate under large tensile loads, detaching the surgical tool 100 from the robotic manipulator can result in a sudden release of built-up tension (backlash) in the drive cables 302a-d, which, in extreme scenarios, can cause the drive housing 108 to eject or launch from the robotic manipulator. As described herein, the cable brake assembly 114 may be manually or computer actuated to bind the drive cables 308a-d and thereby prevent the built-up tension from inadvertently releasing and potentially causing damage to the surgical tool 100 or harm to a nearby user.

The cable brake assembly 114 may be arranged and otherwise provided at a variety of locations on the surgical tool 100. Suitable locations include any location where the cable brake assembly 114 is able to interact with (e.g., engage) one or more of the drive cables 302a-d (FIG. 3). In one embodiment, as illustrated, the cable brake assembly 114 may be coupled to and otherwise arranged in the drive housing 108. In other embodiments, however, the cable brake assembly 114 may alternatively be coupled to and otherwise arranged on the shaft 102 in a variety of locations, as represented by the dashed boxes. In some embodiments, for example, the cable brake assembly referenced as 114' may be positioned at or near the distal end of the shaft 102 and otherwise near the end effector 104. In other embodiments, the cable brake assembly referenced as 114" may be positioned at or near the proximal end of the shaft 102 and otherwise near the drive housing 108. In yet other embodiments, the cable brake assembly 114 may be positioned at an intermediate location between the distal and proximal ends of the shaft 102, without departing from the scope of the disclosure.

Figure 4A:
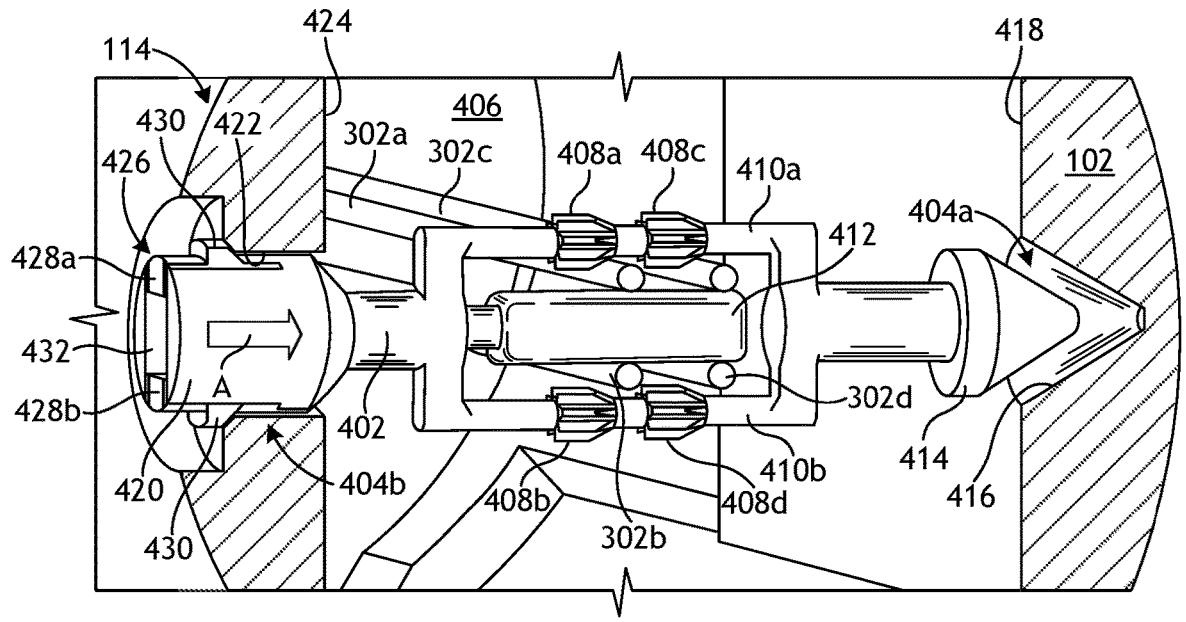
FIGS. 4A and 4B are enlarged cross-sectional side views of an example cable brake assembly.
Figure 4B:
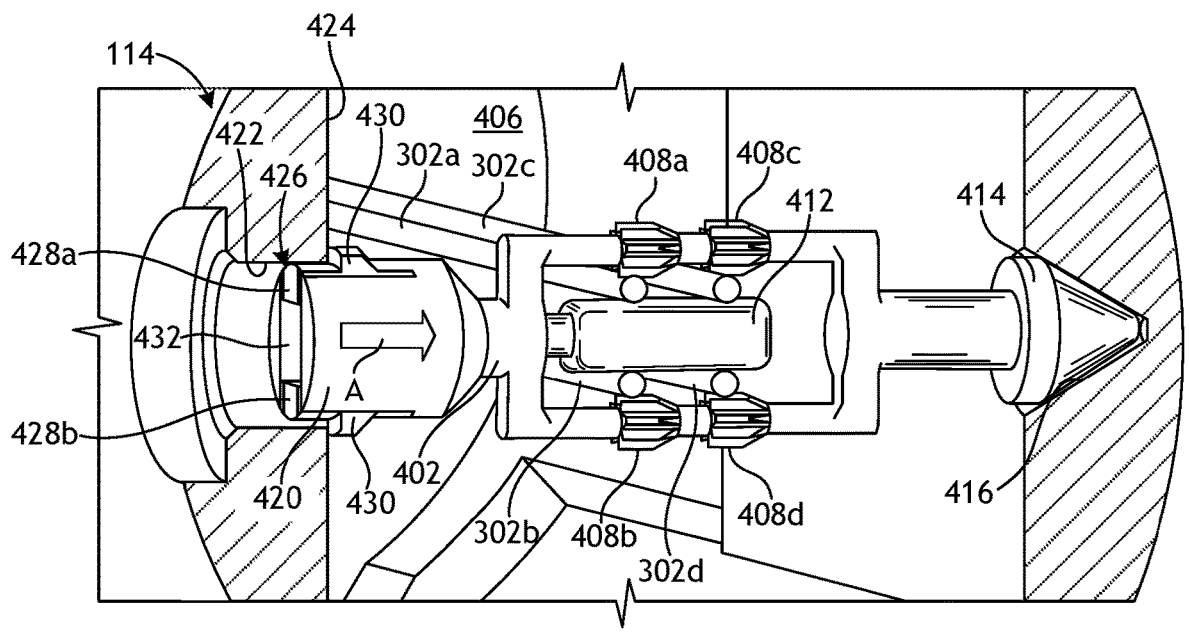

FIGS. 4A and 4B are enlarged, partial cross-sectional side views of an example cable brake assembly 114, according to one or more embodiments. The cable brake assembly 114 (hereafter "the assembly 114") may be actuatable between a first or disengaged position, as shown in FIG. 4A, and a second or braking position, as shown in FIG. 4B. When the assembly 114 is in the first position, the drive cables 302*a-d* are able to longitudinally translate and otherwise operate normally as described above. When the assembly 114 is moved to the braking position, however, portions of the assembly 114 will engage and bind the drive cables 302*a-d* to prevent or mitigate movement (translation) of the drive cables 302*a-d*. Accordingly, moving the assembly 114 to the braking position refers to moving 114 portions of the assembly 114 into contact with the drive cables 302*a-d* to produce sufficient friction and/or interaction forces that prevent the drive cables 302*a-d* from moving or translating relative to the assembly 114.

Referring first to FIG. 4A, the assembly 114 includes a brake chassis 402 that extends transverse to the longitudinal direction of the drive cables 302*a-d*. In at least one embodiment, the brake chassis 402 may extend orthogonal or nearly orthogonal to the longitudinal direction of the drive cables 302*a-d*, but could alternatively extend in a direction that is transverse but not orthogonal to the drive cables 302*a-d*, without departing from the scope of the disclosure.

The brake chassis 402 has a first end 404*a* and a second end 404*b*, and may be primarily positioned within a cavity 406 defined within the surgical tool 100 of FIG. 1. The cavity 406 may be defined or otherwise provided at any site on the surgical tool 100 where the assembly 114 is able to interact with (e.g., engage) one or more of the drive cables 302*a-d*. In the illustrated embodiment, the cavity 406 is located at an axial position along the shaft 102. Accordingly, in at least one embodiment, the cavity 406 may comprise a portion of the lumen 304 (FIG. 3) of the shaft 102. In other embodiments, however, the cavity 406 may be located within the drive housing 108 (FIG. 1) or within a coupling that couples the shaft 102 to the drive housing 108.

The assembly 114 includes one or more brakes engageable with one or more of the drive cables 302*a-c*. In the illustrated embodiment, the assembly 114 includes a first brake 408*a* engageable with the first drive cable 302*a*, a second brake 408*b* engageable with the second drive cable 302*b*, a third brake 408*c* engageable with the third drive cable 302*c*, and a fourth brake 408*d* engageable with the fourth drive cable 302*d*. While the assembly 114 is depicted as providing a one-to-one correspondence between the brakes 408*a-d* and the drive cables 302*a-d*, the assembly 114 may alternatively comprise a single brake configured to engage two or more of the drive cables 302*a-d*, without departing from the scope of the disclosure.

In the illustrated embodiment, the assembly 114 is designed to be actuated to simultaneously engage all of the drive cables 302*a-d* upon actuation to collectively prevent their axial translation. In other embodiments, however, the assembly 114 may instead be configured to independently engage less than all of the drive cables 302*a-d* (or groups of the drive cables 302*a-d*) such that the user determines which of the drive cables 302*a-d* (or groups thereof) is engaged with the cable brake assembly 114.

The brakes 408*a-d* may comprise a variety of structures configured to contact and grippingly engage (i.e., provide a frictional engagement) the corresponding drive cables 302*a-d* when the assembly 114 is actuated. In the illustrated embodiment, for example, the brakes 408*a-d* are depicted as generally cylindrical structures that provide and otherwise define a plurality of gears or teeth operable to engage the outer surface of the corresponding drive cable 302*a-d* upon actuation of the assembly 114. The brakes 408*a-d* may be made of a variety of rigid or semi-rigid materials such as, but not limited to, metal, plastic, a composite material, or any combination thereof. In some embodiments, the brakes 408*a-d* may be made of a material that is rigid or hard enough to dig into and otherwise score the outer surface of the corresponding drive cable 302*a-d* upon actuating the assembly 114.

To accommodate and position the brakes 408*a-d* adjacent the corresponding drive cables 302*a-d*, the brake chassis 402 may include a first leg 410*a* and a second leg 410*b*, where the first and second legs 410*a,b* are laterally offset from each other and extend parallel. As illustrated, the first leg 410*a* supports and otherwise carries the first and third brakes 408*a,c* and the second leg 410*b* supports and otherwise carries the second and fourth brakes 408*b,d*. Those skilled in the art, however, will readily appreciate that a multitude of different structural designs may be employed to arrange the brakes 408*a-d* adjacent the corresponding drive cables 302*a-d*, without departing from the scope of the disclosure. Accordingly, incorporation of the legs 410*a,b* in the brake chassis 402 is merely for illustrative purposes and should not be considered limiting to the present disclosure.

The assembly 114 may further include a brake pad 412 arranged such that one or more of the drive cables 302*a-d* are able to interpose a corresponding one or more of the brakes 408*a-d* and the brake pad 412. In the illustrated embodiment, the brake pad 412 is coupled to and extends from the brake chassis 402 and, therefore, is movable with the brake chassis 402. In other embodiments, however, the brake pad 412 may be separate from the brake chassis 402, such as being coupled to an inner wall of the cavity 406, without departing from the scope of the disclosure.

The brake pad 412 may comprise any rigid support structure that helps facilitate gripping or frictional engagement between the brakes 408*a-d* and the corresponding drive cables 302*a-d*. When the assembly 114 is actuated, as discussed below, the brakes 408*a-d* will engage and drive the drive cables 302*a-d* against and into biased engagement with the brake pad 412. The rigidity of the brake pad 412 enables the brakes 408*a-d* bind the corresponding drive cables 302*a-d* in place such that axial movement in either longitudinal direction is substantially or entirely prevented. In at least one embodiment, the geared or toothed structure provided by the brakes 408*a-d* may be sufficiently hard to dig into and otherwise score the outer surface of the corresponding drive cable 302*a-d*, which helps prevent movement of the drive cables 302*a-d*.

In some embodiments, the assembly 114 may further include a key 414 arranged at the first end 404*a* of the brake chassis 402*a* and configured to be received within a pocket 416 defined in an inner sidewall 418 of the cavity 406. The key 414 may be coupled to the first end 404*a* or may alternatively form an integral part and/or extension of the first end 404a. In the illustrated embodiment, the key 414 comprises a conical member and the pocket 416 is similarly shaped (but in the negative) to receive and seat the first end 404a of the assembly 114. In some embodiments, receiving the key 414 into the pocket 416 may help support the assembly 114 during operation. In other embodiments, as discussed below, receiving the key 414 into the pocket 416 may help prevent the assembly 114 from rotating during operation. In such embodiments, the key 414 and the pocket 416 may comprise any number of mating geometries utilized to counter or resist rotation of the brake chassis 402.

Example operation of the assembly 114 is now provided. The assembly 114 is actuated by placing an axial load on the brake chassis 402 in a direction generally transverse to the longitudinal direction of the drive cables 302a-d, as indicated by the arrow A. In some embodiments, the axial load will move the brake chassis 402 orthogonal (perpendicular) to the longitudinal direction of the drive cables 302a-d. In other embodiments, however, the brake chassis 402 may be configured to articulate in a direction that is transverse but not orthogonal to the drive cables 302a-d, without departing from the scope of the disclosure. Accordingly, actuating the assembly 114 results in the brake chassis 402 moving laterally through the cavity 406 in the direction A and transversely with respect to the drive cables 302a-d.

The axial load required to move the brake chassis 402 may be applied to the assembly 114 at an input module 420. In the illustrated embodiment, the input module 420 is arranged at the second end 404b of the brake chassis 402. The input module 420 may be coupled to the second end 404b or alternatively may form an integral part of the second end 404b, without departing from the scope of the disclosure.

As illustrated, the input module 420 may extend through an aperture 422 defined in a sidewall 424 that defines at least a portion of the cavity 406. In some embodiments, a user (e.g., a surgeon, a clinician, etc.) may provide the required axial load in the direction A by manually engaging the input module 420 with a finger or a tool. In other embodiments, the axial load in the direction A may be automated and otherwise applied to the input module 420 by an actuator or machine configured to engage the input module 420.

In FIG. 4A, the assembly 114 is in the disengaged position, where the brakes 408a-d are not in engagement with the drive cables 302a-d. The brakes 408a-d are laterally spaced from each other on the corresponding legs 410a,b at positions configured to engage the drive cables 302a-d upon actuation of the assembly 114. More specifically, the first and third brakes 408a,c are disposed on the first leg 410a and are laterally spaced from each other such that they are proximate to the first and third drive cables 302a,c, respectively. Similarly, the second and fourth brakes 408b,d are disposed on the second leg 410b and laterally spaced from each other such that they are proximate to the second and fourth drive cables 302b,d, respectively.

In FIG. 4B, the assembly 114 is shown after having been actuated and otherwise moved laterally in the direction A to the braking position, where the brakes 408a-d come into gripping engagement with the corresponding drive cables 302a-d. The key 414 simultaneously advances in the direction A and is received in the pocket 416, which helps center and support the assembly 114 within the cavity 406 when in the braking position. If the assembly 114 includes only two brakes configured to engage two corresponding drive cables, the key 414 may alternatively be ramped or wedge-shaped, without departing from the scope of the disclosure. In some embodiments, the assembly 114 may be actuated in the direction A until the key 414 bottoms out in the pocket 416, which ensures that the assembly 114 has moved a predetermined distance sufficient to have the brakes 408a-d come into gripping engagement with the corresponding drive cables 302a-d.

As the brake chassis 402 and accompanying brake pad 412 move in the direction A, the brakes 408a-d eventually move into contact with the corresponding drive cables 302a-d. In some embodiments, as illustrated, the leading edge of each brake 408a-d may be ramped and/or otherwise angled to help the brakes 408a-d transition over and laterally align with the corresponding drive cables 302a-d. As the brakes 408a-d laterally align with the drive cables 302a-d, the drive cables 302a-d are simultaneously driven against the adjacent outer surface of the brake pad 412, which enables the brakes 408a-d bind the corresponding drive cables 302a-d in place to substantially or entirely prevent axial movement of the cables 302a-d in either axial direction within the cavity 406.

In some embodiments, the assembly 114 may further include a locking assembly 426 used to lock the assembly 114 in the braking position. In some embodiments, the locking assembly 426 may be reversible, thus allowing a user to selectively unlock the assembly 114 from the braking position and return the assembly 114 to the disengaged position. In other embodiments, however, the locking assembly 426 may be non-reversible and instead require disassembly of the assembly 114 to unlock the assembly 114 from the braking position.

In the illustrated embodiment, the locking assembly 426 is arranged at or near the second end 404b of the brake chassis 402 and otherwise forming part of the input module 420. The locking assembly 426 includes one or more locking tabs, shown as a first locking tab 428a and a second locking tab 428b. As will be appreciated, more or less than two locking tabs 428a,b may be employed, without departing from the scope of the disclosure.

Each locking tab 428a,b may comprise an axially extending finger supported at one end and arranged within a slot 432 defined in, for example, the body of the input module 420. A projection 430 is provided on each locking tab 428a,b that helps each locking tab 428a,b operate as a flexible collet finger as the assembly 114 moves in the direction A to the braking position. More specifically, when the assembly 114 is in the disengaged position (FIG. 4A), the projections 430 are located on the exterior of the cavity 406 and outside of the aperture 422. As the brake chassis 402 is moved in the direction A, the projections 430 engage the inner diameter of the aperture 422, which urges the locking tabs 428a,b to flex inward into the slot 432 to pass through the aperture 422 defined in the sidewall 424. In at least one embodiment, as illustrated, the leading edge of the projections 430 may be ramped and otherwise angled to help urge the locking tabs 428a,b to flex inward toward the slot 432 as the locking assembly 426 moves in the direction A.

Upon exiting the aperture 422 within the cavity 406, the projections 430 spring radially outward once more and serve to maintain the assembly 114 in the braking position. In at least one embodiment, for example, the trailing edge of each projection may be flat and otherwise configured to abut against the sidewall 424 of the cavity 406 and thereby prevent the assembly 114 from reversing direction back toward the disengaged position.

Figure 5A:
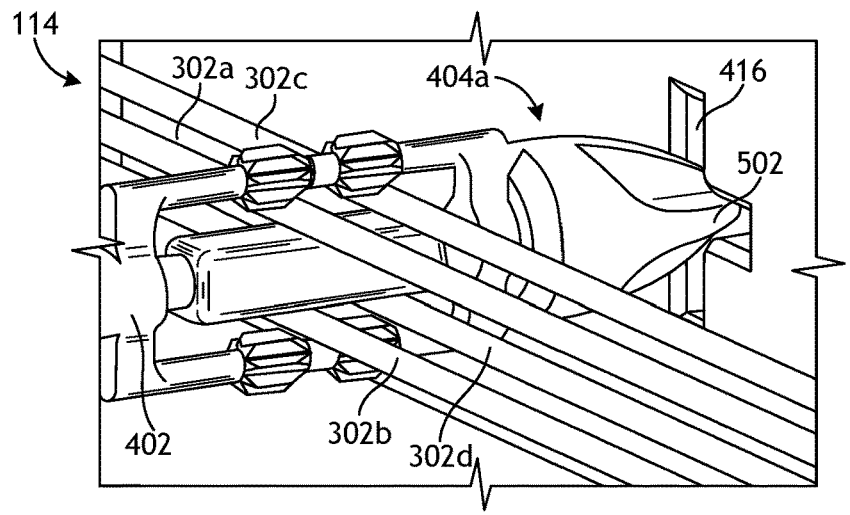
FIGS. 5A, 5B, and 5C are enlarged isometric views of alternative embodiments of the cable brake assembly of FIGS. 4A-4B.
Figure 5B:
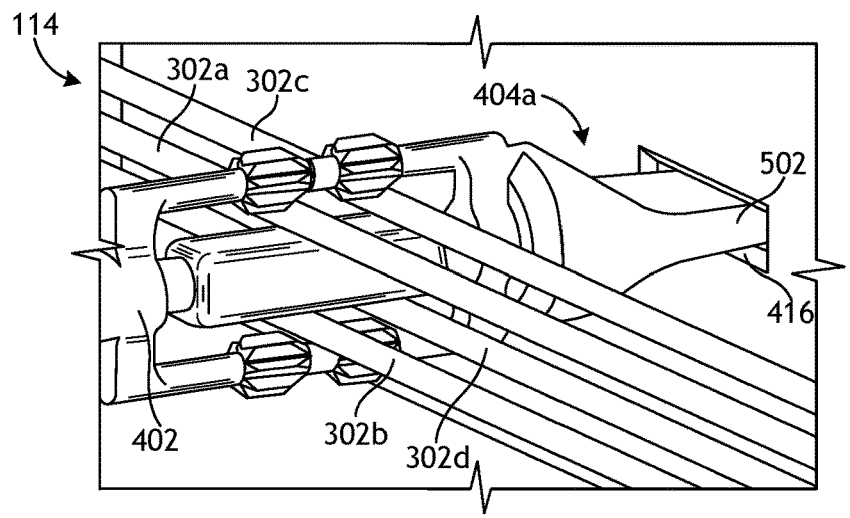
Figure 5C:
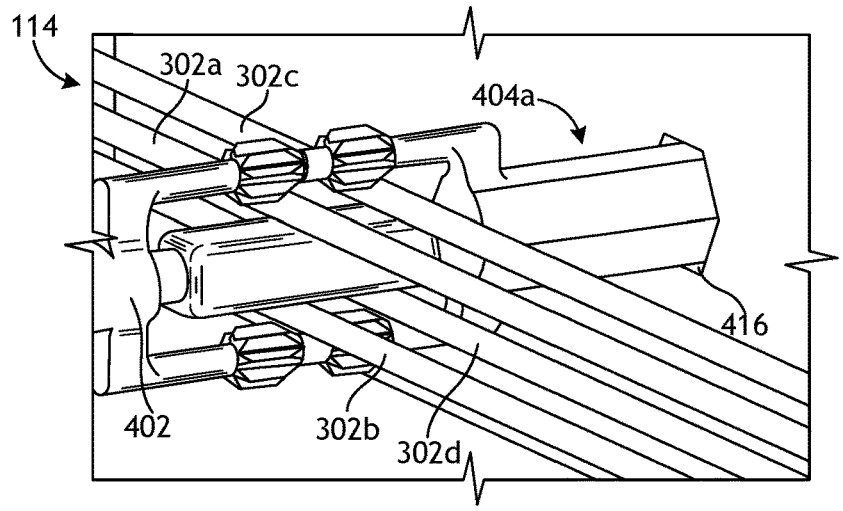

FIGS. 5A, 5B, and 5C are enlarged isometric views of alternative embodiments of the assembly 114 of FIGS. 4A-4B. In some applications, it may be desired to inhibit rotation of the assembly 114 imparted through engagement with the drive cables 302a-d. In some embodiments, rotation of the assembly 114 may be inhibited by mating the first end 404a of the brake chassis 402 with the pocket 416. In some embodiments, the first end 404a itself may mate with the pocket 416 to prevent rotation. In other embodiments, however, a key 502 arranged at the first end 404a may mate with the pocket 416 to prevent rotation. The key 502 may be similar in some respects to the key 414 of FIGS. 4A-4B, and therefore may be best understood with reference thereto.

In FIG. 5A, the key 502 provides a Phillips head geometry configured to be received by and mate with a correspondingly shaped (but in the negative) pocket 416. In FIG. 5B, the key 502 comprises a flat head geometry configured to be received by and mate with a correspondingly shaped (but in the negative) pocket 416. In FIG. 5C, the second end 404a of the brake chassis 402 itself comprises a hex head geometry configured to be received by and mate with a correspondingly shaped (but in the negative) pocket 416.

In each embodiment of FIGS. 5A-5C, the pocket 416 provides a geometry that interferes with the key 502 arranged at the second end 404a (or alternatively the second end 404a itself) to prevent rotation of the brake chassis 402. The pockets 416, however, may provide enough depth to permit translation of the brake chassis 402 to fully actuate the assembly 114, as described above. It will be appreciated, however, that the assembly 114 may be differently configured to inhibit rotation. For example, the second end 404b (FIGS. 4A-4B) of the brake chassis 402 and the aperture 422 (FIGS. 4A-4B) may alternatively be configured with mating geometries (e.g., hex shaped) that prevent rotation, without departing from the scope of the disclosure.

Figure 6:
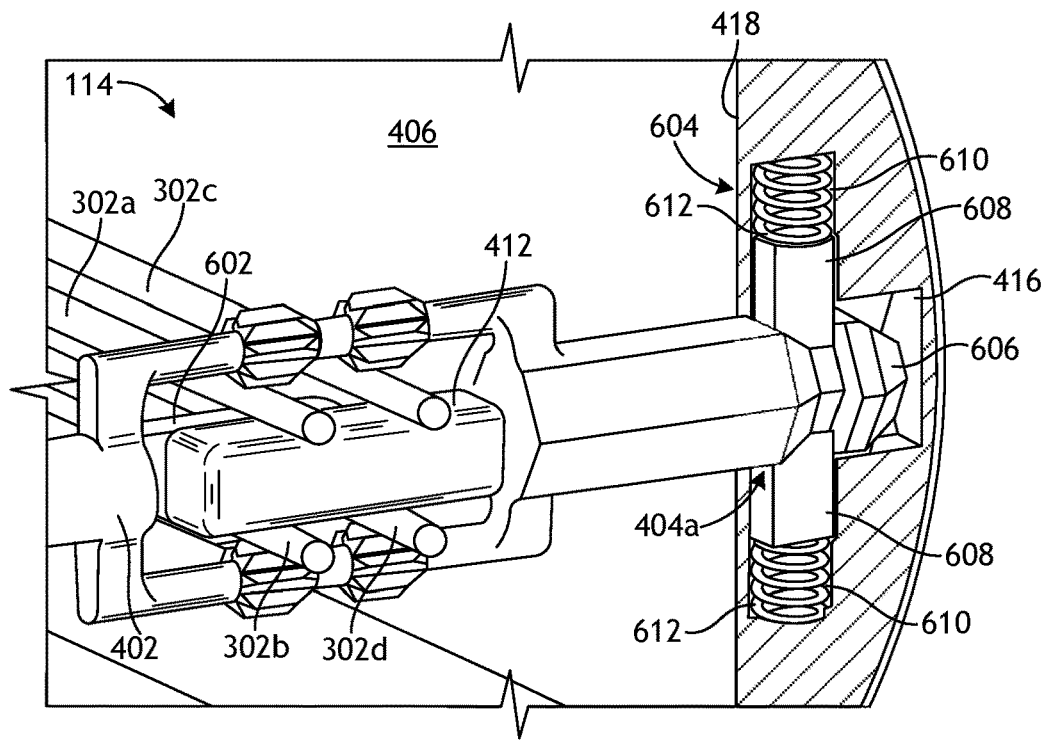
FIG. 6 is an enlarged isometric view of another embodiment of the cable brake assembly of FIGS. 4A-4B.

FIG. 6 is an enlarged isometric view of another embodiment of the assembly 114 of FIGS. 4A-4B. In the illustrated embodiment, the brake pad 412 is mounted independent of the brake chassis 402 such that the brake chassis 402 is able to move relative to the brake pad 412 when the assembly 114 is actuated to the braking position. More specifically, the brake pad 412 is supported within the cavity 406 with a support mount 602 (partially visible) operatively coupled to both the brake pad 412 and a sidewall (not shown) of the cavity 406.

As illustrated, the assembly 114 may further include a locking assembly 604 used to lock the assembly 114 in the braking position. Unlike the locking assembly 426 of FIGS. 4A-4B, the locking assembly 604 is arranged at the first end 404a of the brake chassis 402. As illustrated, the locking assembly 604 includes a bullnose 606 and one or more lugs 608 movable relative to the bullnose 606 and configured to interact with the bullnose 606 to lock the assembly 114 in the braking position. While two lugs 608 are shown in FIG. 6, more or less than two lugs 608 may be employed, without departing from the scope of the disclosure.

The bullnose 606 may be sized to be received within the pocket 416, and the lugs 608 may be arranged within corresponding recesses 610 defined in the sidewall 418 of the cavity 406. As illustrated, the recesses 610 extend from and otherwise communicate with the pocket 416 to enable the lugs 608 to interact with the first end 404a of the brake chassis 402 and, more particularly, with the bullnose 606. In at least one embodiment, the lugs 608 may be biased into engagement with the bullnose 606 with a biasing element 612 (e.g., a coil spring) arranged within each recess 610.

In some embodiments, the first end 404a of the brake chassis 402 and the pocket 416 may exhibit matching cross-sectional geometries. In the illustrated embodiment, for example, the first end 404a of the brake chassis 402 exhibits a hexagonal cross-section, and the pocket 416 may exhibit a corresponding hexagonal cross-section sized to receive the first end 404a. The mating geometries may prove advantageous in helping inhibit rotation of the assembly 114 imparted through engagement with the drive cables 302a-d, as generally described above.

Figure 7A:
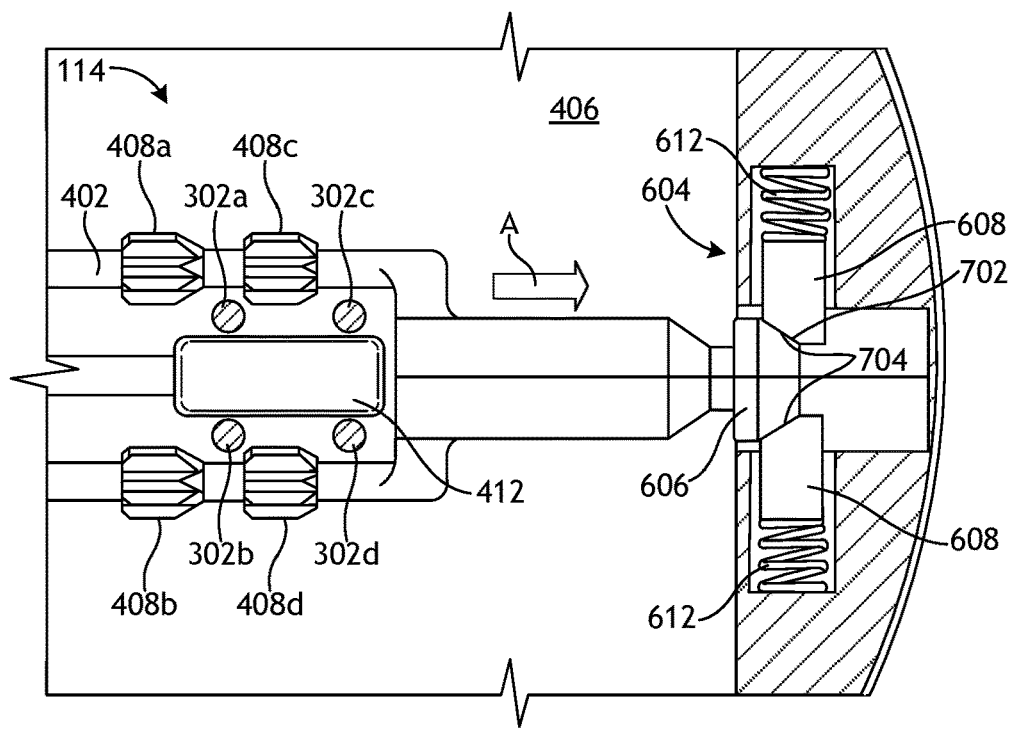
FIGS. 7A-7C are partial cross-sectional side views of the cable brake assembly of FIG. 6 showing example operation.
Figure 7B:
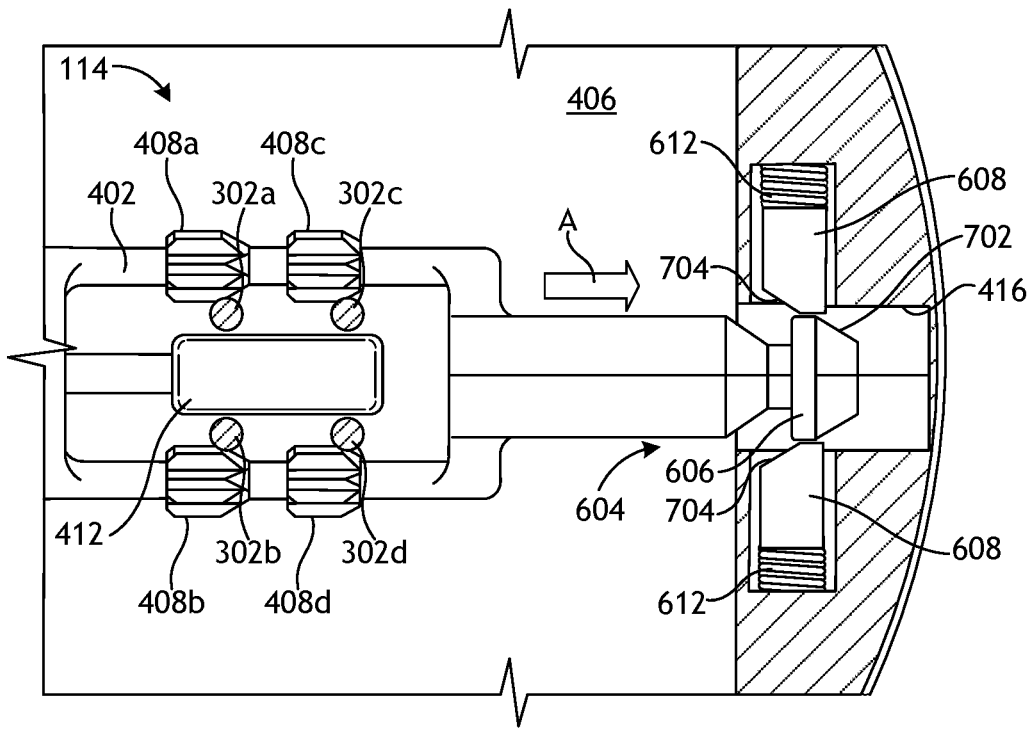
Figure 7C:
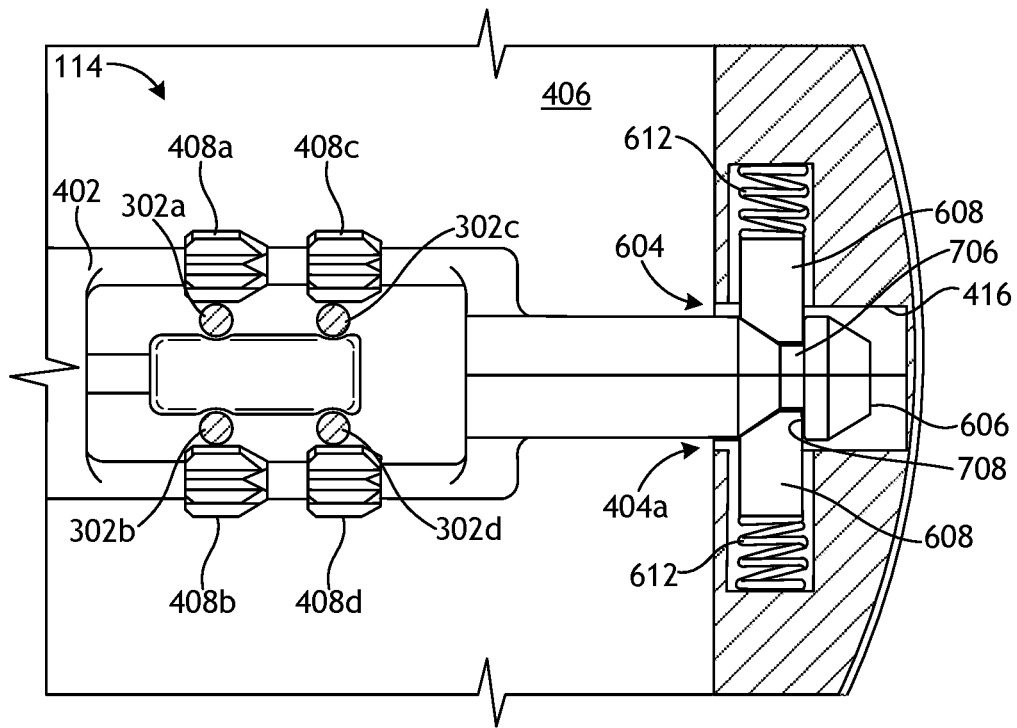

FIGS. 7A-7C are partial cross-sectional side views of the assembly 114 of FIG. 6 showing example operation, according to one or more embodiments. In FIG. 7A, the assembly 114 is in the disengaged position, where the brakes 408a-d are not engaged with the drive cables 302a-d, and where the locking assembly 604 is in an unlocked position. As discussed above, an axial load in the direction A is placed on the brake chassis 402 to actuate the assembly 114, which results in the brake chassis 402 moving laterally through the cavity 406 and transversely with respect to the drive cables 302a-d. Moreover, the brake chassis 402 will move laterally relative to the brake pad 412 also, which, in this embodiment, is fixed to a sidewall of the cavity 406.

The lugs 608 are urged into engagement with the bullnose 606 with the biasing devices 612. As illustrated, the bullnose 606 may provide and otherwise define a ramped leading edge 702 configured to interact with a corresponding ramped profile 704 provided on each lug 608. To advance the assembly 114 to the braking position, the axial force applied in the direction A overcomes the spring force of the biasing devices 612.

In FIG. 7B, the brake chassis 402 is shown having advanced in the direction A. As the brake chassis 402 moves laterally in the direction A the brakes 408a-d eventually come into contact with the corresponding drive cables 302a-d. The brakes 408a-d begin to bind against the drive cables 302a-d as the angled leading edges of each brake 408a-d drive the drive cables 302a-d against the adjacent outer surface of the brake pad 412.

Moreover, moving the brake chassis 402 laterally in the direction A simultaneously advances the bullnose 606 deeper into the pocket 416. As the bullnose 606 advances in the direction A, the leading edge 702 slidingly engages the ramped profile 704 of each lug 608 and overcomes the spring force of the biasing devices 612, which urges the lugs 608 radially outward relative to the bullnose 606. This allows the bullnose 606 to bypass the lugs 608 and advance deeper into the pocket 416.

In FIG. 7C, the assembly 114 is depicted as having moved to the braking position where the brakes 408a-d come into gripping engagement with the corresponding drive cables 302a-d as supported by the brake pad 412. As the brakes 408a-d become laterally aligned with the drive cables 302a-d, the drive cables 302a-d are simultaneously driven against the adjacent (underlying) outer surface of the brake pad 412. In this position, the brakes 408a-d bind the corresponding drive cables 302a-d in place to substantially or entirely prevent axial movement of the cables 302a-d in either axial direction within the cavity 406.

Moreover, when the assembly 114 reaches the braking position, the bullnose 606 will have advanced into the pocket 416 to a point where the lugs 608 are able to be received within a reduced-diameter collar 706 defined on the first end 404a of the brake chassis 402. Once the lugs 608 locate the collar 706, the spring force of the biasing devices 612 may urge the lugs 608 into engagement with the collar 706 and thereby lock the assembly 114 in the braking position.

In the illustrated embodiment, the collar 706 is bounded by a flat trailing edge 708 defined on the backside of the bullnose 606, which engages adjacent flat surfaces of the lugs 606 and thereby prevents the brake chassis 402 from reversing direction. In other embodiments, however, the trailing edge 708 of the bullnose 606 may be ramped or otherwise angled to enable the brake chassis 402 to be reversed in the opposite direction and thereby move the assembly 114 back to the disengaged position. Accordingly, in some embodiments, the locking assembly 604 may be reversible, thus allowing a user to selectively unlock the assembly 114 from the braking position and return the assembly 114 to the disengaged position. In other embodiments, however, the locking assembly 604 may be non-reversible and instead require disassembly of the assembly 114 to unlock the assembly 114 from the braking position.

Figure 8A:
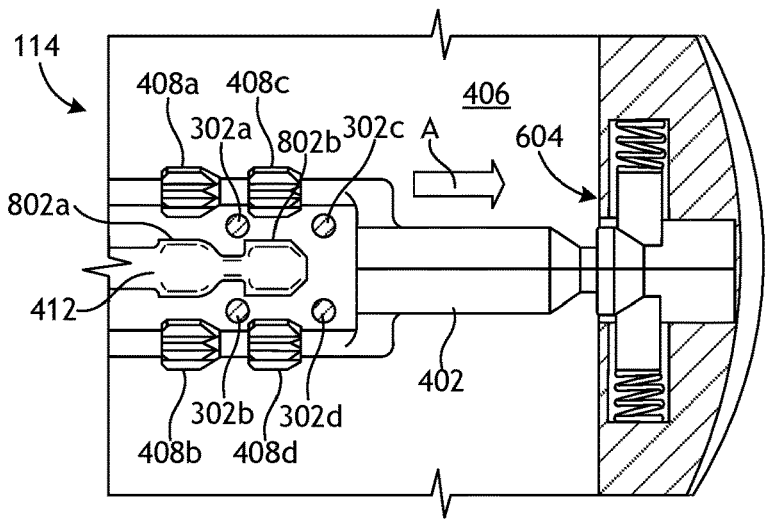
FIGS. 8A-8C are partial cross-sectional side views of an alternative embodiment of the cable brake assembly of FIG. 6 showing example operation.
Figure 8B:
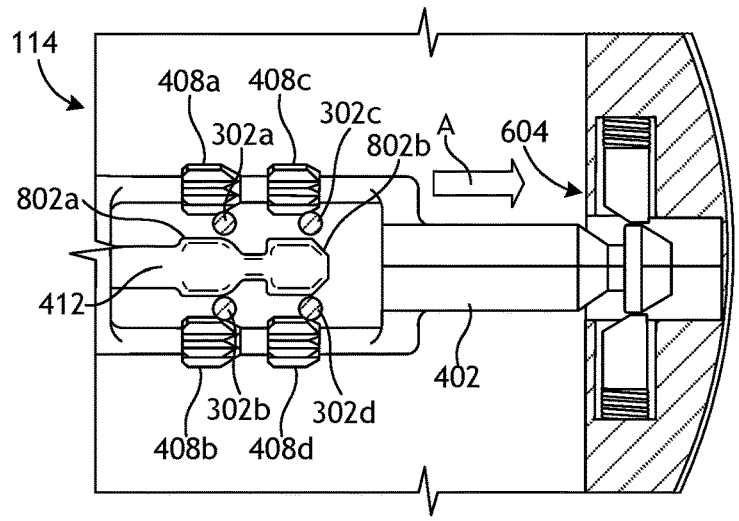
Figure 8C:
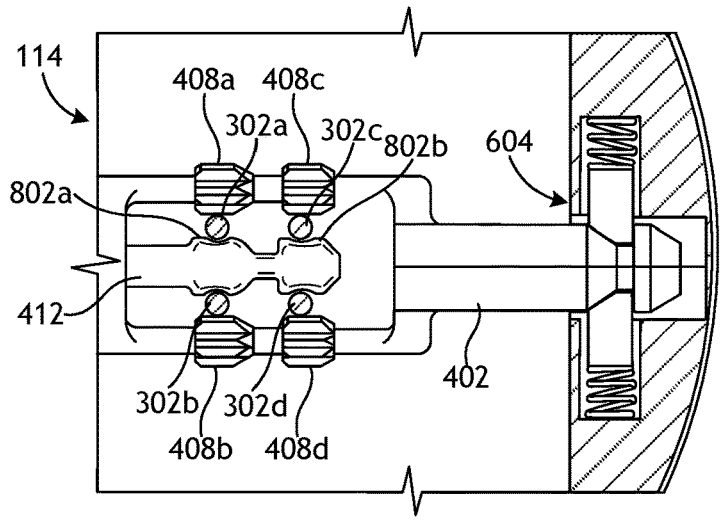

FIGS. 8A-8C are partial cross-sectional side views of an alternative embodiment of the assembly 114 of FIG. 6 and showing progressive, example operation. The assembly 114 in FIGS. 8A-8C is similar to the assembly 114 of FIG. 6 except that it incorporates an alternative embodiment for the brake pad 412.

In the illustrated embodiment, the brake pad 412 is coupled to and extends from the brake chassis 402 and, therefore, is movable with the brake chassis 402 upon actuation of the assembly 114. Moreover, the brake pad 412 provides an outer profile configured to help bind the drive cables 302a-d against longitudinal translation when desired. More specifically, the brake pad 412 may define one or more projections, shown as projections 802a and 802b that extend outward from and otherwise have a larger diameter than the main body of the brake pad 412. In the illustrated embodiment, each projection 802a,b is configured to interact with at least one of the drive cables 302a-d upon actuation of the assembly 114; the first projection 802a interacting with the first and second drive cables 302a,b and the second projection 802b interacting with the third and fourth drive cables 302c,d. While two projections 802a,b are depicted, more or less than two may be employed, without departing from the scope of the disclosure.

Operation of the assembly 114 in FIGS. 8A-8C, including operation of the locking assembly 604, is substantially similar to operation of the assembly 114 as described with reference to FIGS. 7A-7C. In FIG. 8A, the assembly 114 is in the disengaged position where the brakes 408a-d are not engaged with the drive cables 302a-d. An axial load in the direction A is assumed by the brake chassis 402 to actuate the assembly 114, as generally described above, which results in the brake chassis 402 and the brake 412 moving laterally through the cavity 406 and transversely with respect to the drive cables 302a-d.

In FIG. 8B, the brake chassis 402 has advanced in the direction A and the brakes 408a-d have come into initial contact with the corresponding drive cables 302a-d. In some embodiments, the leading edges of each projection 802a,b may be angled and otherwise ramped to help transition the drive cables 302a-d between the projections 802a,b and the opposing brakes 408a-d.

In FIG. 8C, the assembly 114 is moved to the braking position where the brakes 408a-d laterally align with and grippingly engage the corresponding drive cables 302a-d as supported by the underlying brake pad 412 and, more particularly, as supported by the projections 802a,b. In some embodiments, the brake pad 412 or the projections 802a,b may be made of a semi-rigid or malleable material. In such embodiments, as illustrated, driving the drive cables 302a-d against the projections 802a,b may partially deform the projections 802a,b. This may prove advantageous in helping secure the drive cables 302a-d in place to substantially or entirely prevent axial movement of the cables 302a-d in either axial direction within the cavity 406. In applications that include a malleable brake pad 412, a balance of material hardness (durometer) and coefficient of friction may be ascertained. Surface area of contact could potentially increase with a lower durometer brake pad 412, but a change in coefficient of friction would offer more effect.

Figure 9A:
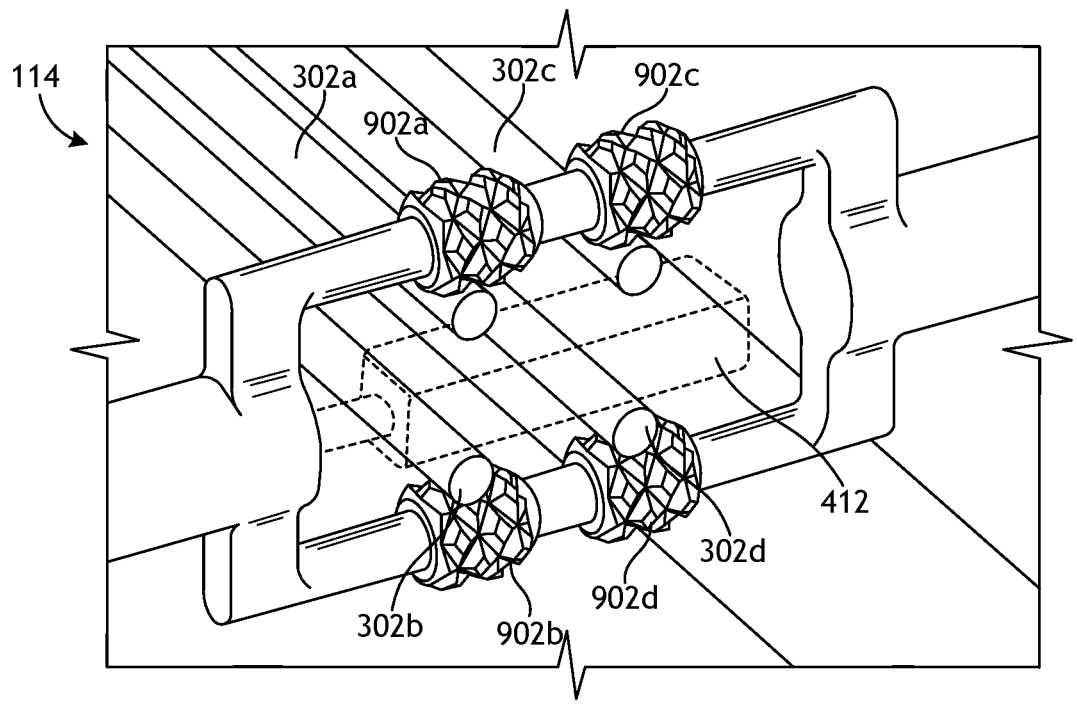
FIGS. 9A and 9B depict alternative brake embodiments that may be used in the cable brake assembly of any of the embodiments described herein.
Figure 9B:
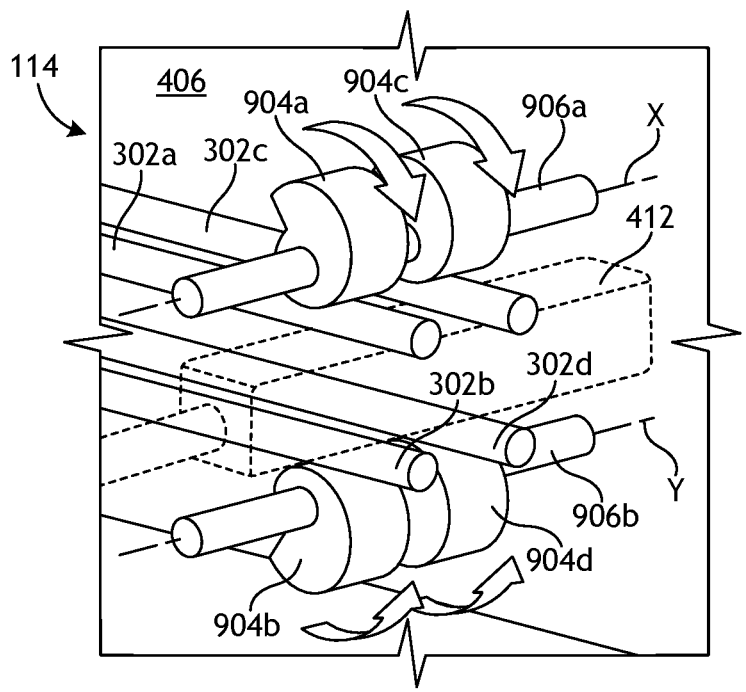

FIGS. 9A and 9B depict alternative brake embodiments that may be used in the assembly 114 of any of the embodiments described herein. As will be appreciated, the assembly 114 described herein may include various types and/or designs of brakes, without departing from the scope of the disclosure. The brakes 408a-d depicted in FIGS. 4A-4B, 5A-5C, 6, 7A-7C, and 8A-8C, for example, comprise non-rotating brakes with gear teeth configured to engage and prevent longitudinal movement of the drive cables 302a-d. In contrast, FIG. 9A depicts brakes 902a, 902b, 902c, and 902d that define a knurled outer surface. The knurled outer surface of each brake 902a-d may be configured to dig into and/or enhance gripping engagement of the drive cables 302a-d as the drive cables 302a-d are urged into contact with the underlying brake pad 412 (shown in dashed lines).

FIG. 9B depicts brakes 904a, 904b, 904c, and 904d in the form of rotatable cams. More specifically, each brake 904a-d is eccentrically shaped to define an enlarged portion that forms a camming surface. Each brake 904a-d may be coupled to a rotatable structure, shown as a first rotatable axle 906a and a second rotatable axle 906b. The first and third brakes 904a,c may be coupled to the first rotatable axle 906a, and the second and fourth brakes 904b,d may be coupled to the second rotatable axle 906b, such that each brake 904a-d rotates simultaneously with the corresponding rotatable axle 906a,b. Each rotatable axle 906a,b may be configured to rotate independent of the other along corresponding centerlines X and Y, respectively. In some embodiments, one of the rotatable axles 906a,b may comprise the brake chassis 402 or one of the legs 410a,b of FIGS. 4A-4B. In other embodiments, each rotatable axle 906a,b may comprise independent rotatable structures suspended for rotation within the cavity 406.

During normal operation of the surgical tool 100 (FIGS. 1 and 3), the brakes 904a-d may be arranged such that the enlarged camming portion of each brake 904a-d is positioned away from the adjacent drive cable 302a-d. Upon actuation of the assembly 114, however, the rotatable axles 906a,b rotate about the corresponding centerlines X, Y, as indicated by the arrows. As the rotatable axles 906a,b rotate, the brakes 904a-d correspondingly rotate and the enlarged camming portion of each cam-shaped brake 904a-d progressively urges the adjacent drive cables 302a-d into contact and gripping engagement with the underlying brake pad 412 (shown in dashed lines), which effectively prevents longitudinal movement of the drive cables 302a-d in either axial direction.

Figure 10:
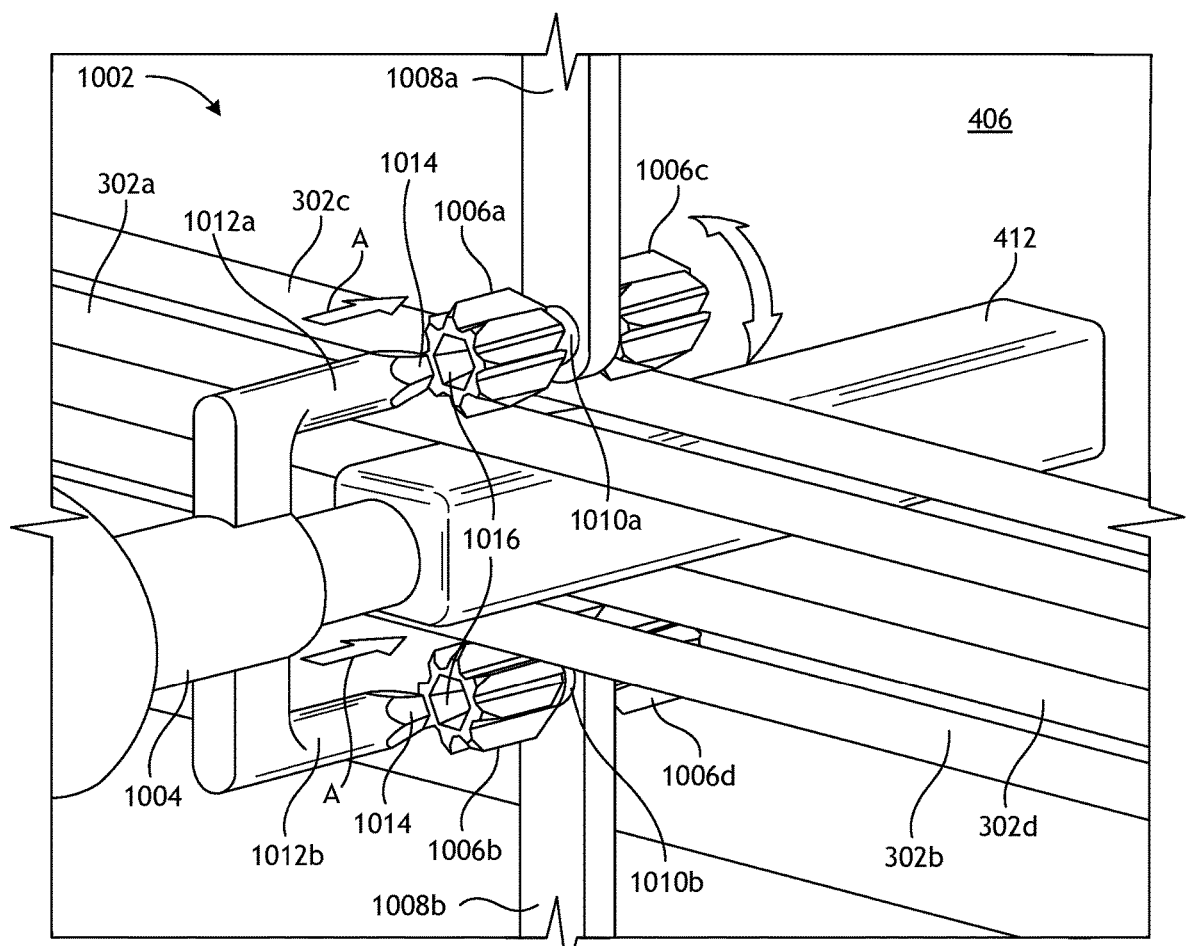
FIG. 10 is an enlarged isometric view of another example cable brake assembly.

FIG. 10 is an enlarged isometric view of another example cable brake assembly 1002, according to one or more embodiments. The cable brake assembly 1002 (hereafter "the assembly 1002") may be substantially similar to the assembly 114 of FIGS. 4A and 4B and therefore may be best understood with reference thereto, where like numerals will represent like elements not described again in detail. Similar to the assembly 114 of FIGS. 4A and 4B, the assembly 1002 may be actuatable between a first or disengaged position, where the drive cables 302a-d are able to longitudinally translate and otherwise operate normally as described herein, and a second or braking position, where portions of the assembly 1002 will engage and bind the drive cables 302a-d to prevent or mitigate movement (translation) of the drive cables 302a-d.

As illustrated, the assembly 1002 includes a brake chassis 1004 that extends generally transverse to the longitudinal direction of the drive cables 302a-d. The brake chassis 1004 is movable in the direction A upon actuation of the assembly 1002. The assembly 1002 may also include one or more brakes engageable with one or more of the drive cables 302a-c. In the illustrated embodiment, the assembly 1002 includes a first brake 1006a engageable with the first drive cable 302a, a second brake 1006b engageable with the second drive cable 302b, a third brake 1006c engageable with the third drive cable 302c, and a fourth brake 1006d engageable with the fourth drive cable 302d.

Each brake 1006a-d may be coupled to an axle that is rotatably mounted to a support attached to the sidewall of the cavity 406. More specifically, the first and third brakes 1006a,c may be coupled to a first axle 1010a rotatably mounted to a first support 1008a, and the second and fourth brakes 1006b,d may be coupled to a second axle 1010b rotatably mounted to a second support 1008b. Accordingly, the first and third brakes 1006a,c may be configured to rotate in tandem, and the second and fourth brakes 1006b,d may configured to rotate in tandem. In other embodiments, however, each brake 1006a-d may be mounted to an independent axle, without departing from the scope of the disclosure. In some embodiments, the supports 1008a,b may be coupled to an inner sidewall of the cavity 406.

The brakes 1006a-d are laterally spaced from each other on the corresponding axles 1010a,b at positions configured to engage the drive cables 302a-d. While the assembly 1002 is depicted as providing a one-to-one correspondence between the brakes 1006a-d and the drive cables 302a-d, the assembly 1002 may alternatively comprise a single brake configured to engage two or more of the drive cables 302a-d, without departing from the scope of the disclosure.

The brakes 1006a-d may be similar to the brakes 408a-d depicted in FIGS. 4A-4B, 5A-5C, 6, 7A-7C, and 8A-8C. In other embodiments, however, the brakes 1006a-d may comprise any of the brakes described herein or any structure capable of grippingly engaging the adjacent drive cables 302a-d upon actuation of the assembly 1002.

The brake chassis 1004 may include a first leg 1012a and a second leg 1012b, where the first and second legs 1012a,b are laterally offset from each other. Each leg 1012a,b may terminate with a key 1014 configured to matingly engage a corresponding profile 1016 provided by one of the brakes 1006a-d in a male-female mating relationship. Upon mating the key 1014 with the profile 1016, the corresponding brake 1006a-d will be prevented from rotating. In the illustrated embodiment, the key 1014 and corresponding profile 1016 comprise mating hexagonal cross-sections. As will be appreciated, however, any number of alternative mating configurations may be employed to accomplish the same purpose, without departing from the scope of the disclosure.

The assembly 1002 may further include the brake pad 412 arranged such that the drive cables 302a-d are able to interpose the brake pad 412 and the brakes 1006a-d. In the illustrated embodiment, the brake pad 412 is coupled to and extends from the brake chassis 1004 and, therefore, is movable with the brake chassis 1004. In other embodiments, however, the brake pad 412 may be coupled to an inner wall of the cavity 406, without departing from the scope of the disclosure.

Prior to actuation of the assembly 1002, the brakes 1006a-d are able to rotate freely on their respective axles 1010a,b and are in contact with the drive cables 302a-d. The assembly 1002 is actuated by placing an axial load on the brake chassis 1004 in the direction A, which is generally transverse to the longitudinal direction of the drive cables 302a-d. The axial load required to move the brake chassis 1004 may be applied to the assembly 1002 as described above with respect to the assembly 114 (FIGS. 4A-4B).

The assembly 1002 is depicted in FIG. 10 in the disengaged position, where the brakes 1006a-d are free to rotate as the drive cables 302a-d translate longitudinally. Actuating the assembly 1102 and thereby moving the brake chassis 1004 in the direction A, however, will eventually mate the keys 1014 with the corresponding profiles 1016 and thereby stop rotation of the brakes 1006a-d. Stopping rotation of the brakes 1006a-d will allow the brakes 1006a-d to grippingly engage the corresponding drive cables 302a-d as supported by the underlying brake pad 412, which prevents the drive cables 302a-d from moving longitudinally in either axial direction.

Figure 11:
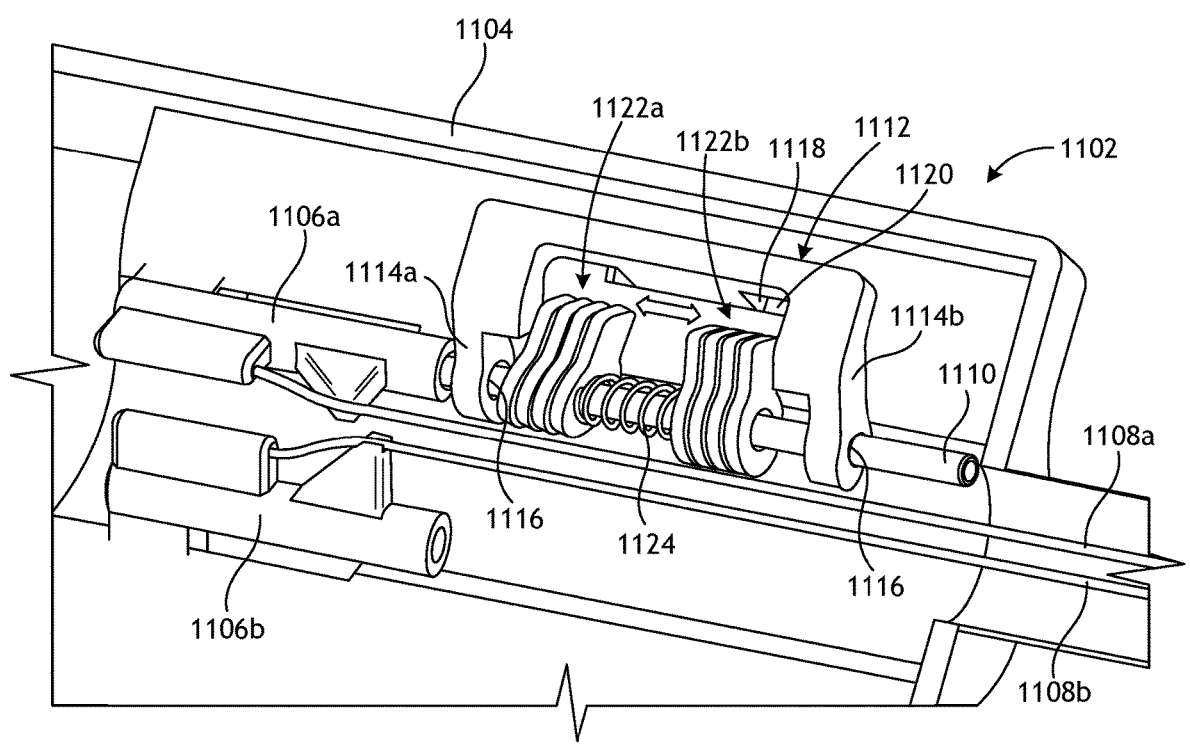
FIG. 11 is an enlarged isometric view of another example cable brake assembly.

FIG. 11 is an enlarged isometric view of another example cable brake assembly 1102, according to one or more embodiments. Similar to the other cable brake assemblies described herein, the cable brake assembly 1102 (hereafter "the assembly 1102") may be selectively actuated to prevent unintentional movement (translation) of drive cables used within a surgical tool (e.g., the surgical tool 100 of FIG. 1). As illustrated, the assembly 1102 may be arranged within a drive housing 1104 of the surgical tool. The drive housing 1104 may be similar to or the same as the drive housing 108 of FIG. 1. A portion of the drive housing 1104 is removed to expose the various component parts of the assembly 1102.

The drive housing 1104 may house one or more input drives, shown as a first input drive 1106a and a second input drive 1106b. The first input drive 1106a may be operatively coupled to a first drive cable 1108a and the second input drive 1106b may be operatively coupled to a second drive cable 1108b, where the drive cables 1108a,b are similar to the drive cables 302a-d described herein. Each input drive 1106a,b may be configured to interact and otherwise interface with a corresponding output drive (not shown) of a tool driver (not shown). More specifically, actuation of a given output drive will move the associated input drive 1106a,b, which correspondingly moves the associated drive cable 1108a,b longitudinally. While only two input drives 1106a,b and corresponding drive cables 1108a,b are depicted in FIG. 11, it will be appreciated that more or less than two may be arranged within the drive housing 1104, without departing from the scope of the disclosure.

In the illustrated embodiment, the assembly 1102 is mounted within the drive housing 1104 and may be actuatable and otherwise operable to help prevent unintentional movement (translation) of the first drive cable 1108a. While not shown, another similar cable brake assembly may be mounted within the drive housing 1104 to help prevent unintentional movement (translation) of the second drive cable 1108b. Accordingly, while the following discussion focuses on actuation and interaction of the assembly 1102 with the first input drive 1106a and the first drive cable 1108a, the principles are equally applicable to actuation and interaction of a similar cable brake assembly (not shown) used in conjunction with the second input drive 1106b and the second drive cable 1108b.

The first drive input 1106a includes a driver rod 1110 that extends longitudinally from the first drive input 1106a. The driver rod 1110 may be coupled to or otherwise form an integral extension of the first drive input 1106a such that actuation of the first drive input 1106a correspondingly moves the driver rod 1110 in the same direction. The assembly 1102 may be operatively mounted to the drive rod 1110. More specifically, the assembly 1102 includes a brake chassis 1112 (alternately referred to as a "carriage") mounted to the driver rod 1110, and the brake chassis 1112 includes a first leg 1114a and a second leg 1114b. The drive rod 1110 extends through an aperture 1116 defined in each leg 1114a,b. The apertures 1116 are large enough such that the driver rod 1110 is able to translate relative to the first and second legs 1114a,b without the brake chassis 1112 binding against the outer surface of the driver rod 1110 and thereby restricting its movement.

The brake chassis 1112 also includes an input module 1118 that extends from the main body of the brake chassis 1112 and through an aperture 1120 defined in the sidewall of the driver housing 1104. In some embodiments, the input module 1118 may be coupled to the brake chassis 1112, but may otherwise form an integral extension thereof. In some embodiments, as illustrated, the input module 1118 may comprise a tab or extension that extends through the aperture 1120, but could alternatively comprise another rigid member, without departing from the scope of the disclosure.

The input module 1118 extends through the aperture 1120 such that it can be manipulated or moved longitudinally on the exterior of the driver housing 1104, as indicated by the directional arrow. Manipulating or moving the input module 1118 longitudinally correspondingly moves the brake chassis 1112 in the same direction. As described below, moving the brake chassis 1112 relative to the driver rod 1110 may result in the assembly 1102 locking down on the driver rod 1110 to prevent the first input driver 1106a from moving, and thereby preventing the first drive cable 1108a from translating longitudinally.

The assembly 1102 also includes one or more locking tabs, shown as a first set of locking tabs 1122a and a second set of locking tabs 1122b. While each set of locking tabs 1122a,b includes four discrete locking tabs, more or less than four may be employed, without departing from the scope of the disclosure. The locking tabs 1122a,b may be mounted to the driver rod 1110 and positioned between the first and second legs 1114a,b. In some embodiments, as illustrated, the driver rod 1110 may extend through coaxially aligned holes defined in each locking tab 1122a,b. The holes are large enough such that the driver rod 1110 may translate relative to the locking tabs 1122a,b without the locking tabs 1122a,b binding against the outer surface of the driver rod 1110 until the assembly 1102 is actuated.

A biasing device 1124 may be arranged between the first and second sets of locking tabs 1122a,b. The biasing device 1124 may comprise, for example, a helical compression spring that extends about the outer surface of the driver rod 1110. In operation, the biasing device 1124 may be configured to help maintain a separation distance between the first and second sets of locking tabs 1122a,b and help keep the locking tabs 1122a,b substantially erect during normal operation. The biasing device 1124 may comprise any other type of biasing mechanism that may be designed to maintain the separation distance between the first and second sets of locking tabs 1122a,b.

During normal operation, the biasing device 1124 helps keep the locking tabs 1122a,b in an upright position so that the locking tabs 1122a,b do not "lean" relative to the drive rod 1110 and otherwise bind against the outer surface of the driver rod 1110. With the locking tabs 1122a,b in the upright (erect) position, the driver rod 1110 is able to freely translate longitudinally in either direction relative to the brake chassis 1112 and the locking tabs 1122a,b.

When it is desired to lock the first drive cable 1108a in position such that it cannot move axially, the input module 1118 may be manipulated (moved) in an axial direction relative to the drive housing 1104. In some embodiments, for example, a user (e.g., a surgeon, a clinician, etc.) may engage the input module 1118 on the exterior of the drive housing 1104 with a finger or a tool and move the input module 1118 distally or proximally, as shown by the directional arrow. In other embodiments, manipulation of the input module 1118 may be automated and otherwise applied by an actuator or machine configured to engage the input module 1118.

Moving the input module 1118 proximally or distally correspondingly moves the brake chassis 1112 along the driver rod 1110. Depending on the direction of movement, the first or second legs 1114a,b will engage the first or second sets of locking tabs 1122a,b and force the corresponding locking tabs 1122a,b into binding engagement with the driver rod 1110. Once the locking tabs 1122a,b come into binding engagement with the driver rod 1110, the first input driver 1106a will be unable to move longitudinally in the opposite direction, which correspondingly prevents the first drive cable 1108a from translating axially in that direction. Accordingly, the assembly 1102 may be manually or computer actuated to bind the first drive cable 1108a and thereby prevent any built-up tension from inadvertently releasing and potentially causing damage to the surgical tool or harm to a nearby user.

Figure 12A:
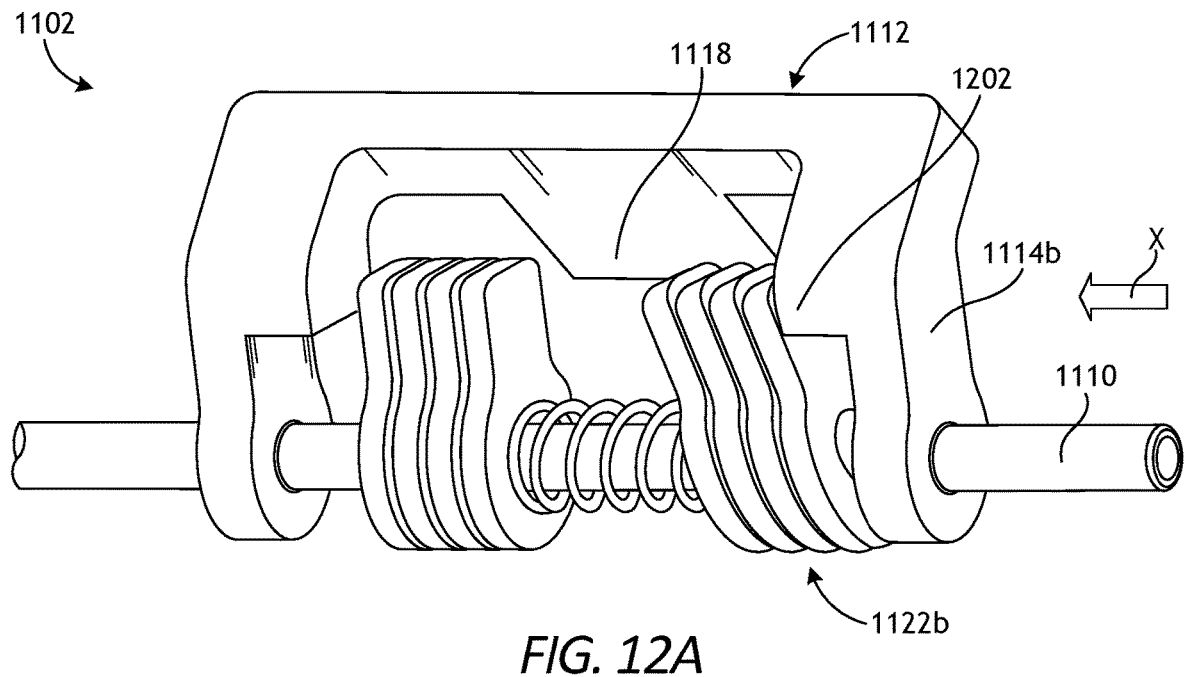
FIGS. 12A and 12B are enlarged views of the assembly of FIG. 11 during example operation.
Figure 12B:
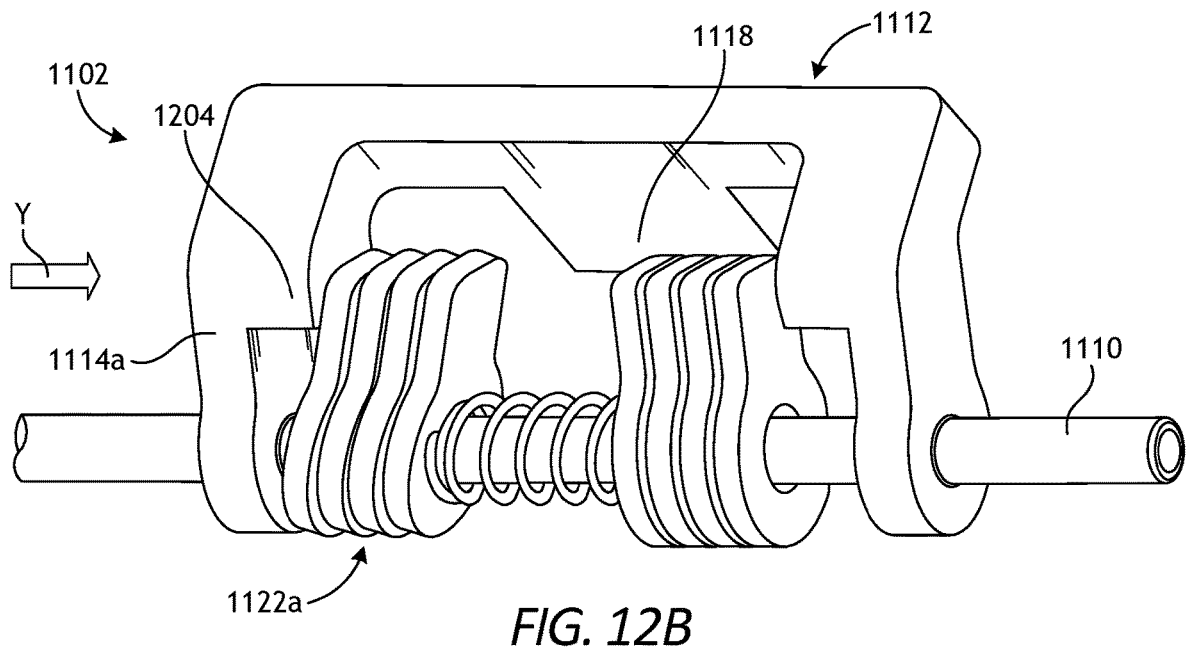

FIGS. 12A and 12B are enlarged views of the assembly 1102 of FIG. 11 during example operation. In FIG. 12A, the brake chassis 1112 is depicted as being moved in a proximal direction X relative to the driver rod 1110. As the input module 1118 is manipulated (moved) in the proximal direction X, the brake chassis 1112 correspondingly moves in the same direction and the second leg 1114b eventually comes into contact with the second set of locking tabs 1122b. The second leg 1114b provides and otherwise defines a protruding shoulder 1202 that engages and causes the second set of locking tabs 1122b to tilt relative to the driver rod 1110, which helps the locking tabs 1122b bind against the outer surface of the driver rod 1110.

Binding the locking tabs 1122b against the driver rod 1110 will prevent the driver rod 1110 from moving in a direction opposite the proximal direction X without correspondingly moving the brake chassis 1112. Moreover, since the input module 1118 extends through the aperture 1120 (FIG. 11), the brake chassis 1112 is prevented from moving past the confines of the aperture 1120. Consequently, the first input driver 1106a (FIG. 11) and the first drive cable 1108a (FIG. 11) are prevented from similarly translating axially in that direction.

FIG. 12B depicts the brake chassis 1112 being moved in a distal direction Y relative to the driver rod 1110. As the input module 1118 is manipulated (moved) in the distal direction Y, the brake chassis 1112 correspondingly moves in the same direction and the first leg 1114a eventually comes into contact with the first set of locking tabs 1122a. More specifically, the first leg 1114a provides and otherwise defines a protruding shoulder 1204 that engages and forces the first set of locking tabs 1122a to tilt relative to the driver rod 1110 and thereby bind against the outer surface of the driver rod 1110. Binding the locking tabs 1122a against the driver rod 1110 will prevent the driver rod 1110 from moving in a direction opposite the distal direction Y, which correspondingly prevents the first input driver 1106a (FIG. 11) and the first drive cable 1108a (FIG. 11) from similarly translating axially in that direction.

Embodiments disclosed herein include:

A. A surgical tool that includes a drive housing, an elongate shaft that extends from the drive housing, a plurality of drive cables extending within the elongate shaft between the drive housing and an end effector coupled to a distal end of the elongate shaft, and a cable brake assembly at least partially arranged within a cavity defined in the drive housing or the elongate shaft, the cable brake assembly having one or more brakes and a brake pad engageable with one or more of the plurality of drive cables, wherein the cable brake assembly is actuatable between a first position, where the plurality of drive cables are free to move longitudinally within the elongate shaft, and a second position, where the one or more brakes and the brake pad engage and prevent the one or more of the plurality of drive cables from moving.

B. A method of operating a surgical tool that includes triggering actuation of one or more actuation devices in a drive housing and thereby moving a plurality of drive cables extending within an elongate shaft extending from the drive housing to an end effector coupled to a distal end of the elongate shaft, actuating a cable brake assembly from a first position, where the plurality of drive cables are free to move longitudinally within the elongate shaft, and to a second position, where one or more brakes and a brake pad of the cable brake assembly engage and prevent the one or more of the plurality of drive cables from moving, wherein the cable brake assembly is at least partially arranged within a cavity defined in the drive housing or the elongate shaft.

C. A cable brake assembly for a surgical tool operable with a plurality of drive cables, the cable brake assembly including a brake chassis, one or more brakes engageable with one or more of the plurality of drive cables, and a brake pad engageable with one or more of the drive cables, wherein the brake chassis is movable between a first position, where the plurality of drive cables are free to move longitudinally within the elongate shaft, and a second position, where the one or more brakes and the brake pad engage and prevent the one or more of the plurality of drive cables from moving.

Each of embodiments A, B, and C may have one or more of the following additional elements in any combination: Element 1: wherein the cable brake assembly further includes a brake chassis and the one or more brakes are arranged on the brake chassis, and wherein the brake chassis is movable in a direction transverse to a longitudinal direction of the plurality of drive cables to laterally align the one or more brakes with the one or more of the plurality of drive cables. Element 2: wherein the brake chassis includes a first leg and a second leg, and wherein at least one of the one or more brakes is arranged on each of the first and second legs. Element 3: wherein an end of the brake chassis is receivable within a pocket defined in an inner sidewall of the cavity upon actuation of the cable brake assembly. Element 4: further comprising a key arranged at the end and matable with the pocket to prevent the brake chassis from rotating. Element 5: further comprising a locking assembly arranged at an end of the brake chassis to lock the cable brake assembly in the second position. Element 6: wherein the locking assembly comprises one or more locking tabs having a projection formed thereon, and wherein the one or more locking tabs flex inward as the cable brake assembly moves to the second position. Element 7: wherein the locking assembly comprises a bullnose provided at the end of the brake chassis and receivable into a pocket defined in a sidewall of the cavity, and one or more lugs arranged within corresponding recesses defined in the sidewall and movable relative to the bullnose to lock the assembly in the second position. Element 8: wherein the one or more lugs are spring-loaded. Element 9: wherein the one or more brakes are selected from the group consisting of a geared or toothed structure, a rotatable cam, and a structure having a knurled outer surface. Element 10: wherein the brake pad provides an outer profile comprising one or more projections engageable with the one or more of the plurality of drive cables. Element 11: wherein the cable brake assembly comprises at least one support attached to a sidewall of the cavity, wherein the one or more brakes are rotatably mounted to the at least one support at an axle, and a brake chassis movable in a direction transverse to a longitudinal direction of the plurality of drive cables and including a leg that terminates with a key matable with a profile provided on the one or more brakes, wherein the key mates with the profile upon actuating the cable brake assembly to the second position to prevent rotation of the one or more brakes on the axle.

Element 12: wherein the cable brake assembly further includes a brake chassis and the one or more brakes are arranged on the brake chassis, and wherein actuating the cable brake assembly comprises moving the brake chassis in a direction transverse to a longitudinal direction of the plurality of drive cables, and laterally aligning the one or more brakes with the one or more of the plurality of drive cables. Element 13: wherein actuating the cable brake assembly further comprises receiving an end of the brake chassis within a pocket defined in an inner sidewall of the cavity. Element 14: further comprising mating a key arranged at the end with the pocket and thereby preventing the brake chassis from rotating. Element 15: wherein laterally aligning the one or more brakes with the one or more of the plurality of drive cables comprises driving the one or more of the plurality of drive cables against an adjacent outer surface of the brake pad with the one or more brakes, and binding the one or more of the plurality of drive cables in place with the one or more brakes to prevent axial movement of the one or more of the plurality of drive cables. Element 16: further comprising locking the cable brake assembly in the second position with a locking assembly arranged at an end of the brake chassis. Element 17: wherein the cable brake assembly includes at least one support attached to a sidewall of the cavity and having the one or more brakes rotatably mounted thereto at an axle, and further includes a brake chassis including a leg that terminates with a key matable with a profile provided on the one or more brakes, and wherein actuating the cable brake assembly comprises moving the brake chassis in a direction transverse to a longitudinal direction of the plurality of drive cables, mating the key with the profile and thereby preventing rotation of the one or more brakes on the axle, and binding the one or more of the plurality of drive cables in place with the one or more brakes to prevent axial movement of the one or more of the plurality of drive cables.

By way of non-limiting example, exemplary combinations applicable to A, B, and C include: Element 1 with Element 2; Element 1 with Element 3; Element 3 with Element 4; Element 1 with Element 5; Element 5 with Element 6; Element 5 with Element 7; Element 7 with Element 8; Element 12 with Element 13; Element 13 with Element 14; and Element 12 with Element 15.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
   a drive housing;
   an elongate shaft that extends from the drive housing;
   a plurality of drive cables extending within the elongate shaft between the drive housing and an end effector coupled to a distal end of the elongate shaft; and
   a cable brake assembly at least partially arranged within a cavity defined in the drive housing or the elongate shaft, the cable brake assembly having one or more brakes and a brake pad engageable with one or more of the plurality of drive cables,
   wherein the cable brake assembly is actuatable between a first position, where the plurality of drive cables are free to move longitudinally within the elongate shaft, and a second position, where the one or more brakes and the brake pad engage and prevent the one or more of the plurality of drive cables from moving.

2. The surgical tool of claim 1, wherein the cable brake assembly further includes a brake chassis and the one or more brakes are arranged on the brake chassis, and wherein the brake chassis is movable in a direction transverse to a longitudinal direction of the plurality of drive cables to laterally align the one or more brakes with the one or more of the plurality of drive cables.

3. The surgical tool of claim 2, wherein the brake chassis includes a first leg and a second leg, and wherein at least one of the one or more brakes is arranged on each of the first and second legs.

4. The surgical tool of claim 2, wherein an end of the brake chassis is receivable within a pocket defined in an inner sidewall of the cavity upon actuation of the cable brake assembly.

5. The surgical tool of claim 4, further comprising a key arranged at the end and matable with the pocket to prevent the brake chassis from rotating.

6. The surgical tool of claim 2, further comprising a locking assembly arranged at an end of the brake chassis to lock the cable brake assembly in the second position.

7. The surgical tool of claim 6, wherein the locking assembly comprises one or more locking tabs having a projection formed thereon, and wherein the one or more locking tabs flex inward as the cable brake assembly moves to the second position.

8. The surgical tool of claim 6, wherein the locking assembly comprises:
   a bullnose provided at the end of the brake chassis and receivable into a pocket defined in a sidewall of the cavity; and
   one or more lugs arranged within corresponding recesses defined in the sidewall and movable relative to the bullnose to lock the assembly in the second position.

9. The surgical tool of claim 8, wherein the one or more lugs are spring-loaded.

10. The surgical tool of claim 1, wherein the one or more brakes are selected from the group consisting of a geared or toothed structure, a rotatable cam, and a structure having a knurled outer surface.

11. The surgical tool of claim 1, wherein the brake pad provides an outer profile comprising one or more projections engageable with the one or more of the plurality of drive cables.

12. The surgical tool of claim 1, wherein the cable brake assembly comprises:
   at least one support attached to a sidewall of the cavity, wherein the one or more brakes are rotatably mounted to the at least one support at an axle; and
   a brake chassis movable in a direction transverse to a longitudinal direction of the plurality of drive cables and including a leg that terminates with a key matable with a profile provided on the one or more brakes,
   wherein the key mates with the profile upon actuating the cable brake assembly to the second position to prevent rotation of the one or more brakes on the axle.

13. A method of operating a surgical tool, comprising:
   triggering actuation of one or more actuation devices in a drive housing and thereby moving a plurality of drive cables extending within an elongate shaft extending from the drive housing to an end effector coupled to a distal end of the elongate shaft;
   actuating a cable brake assembly from a first position, where the plurality of drive cables are free to move longitudinally within the elongate shaft, and to a second position, where one or more brakes and a brake pad of the cable brake assembly engage and prevent the one or more of the plurality of drive cables from moving,
   wherein the cable brake assembly is at least partially arranged within a cavity defined in the drive housing or the elongate shaft.

14. The method of claim 13, wherein the cable brake assembly further includes a brake chassis and the one or more brakes are arranged on the brake chassis, and wherein actuating the cable brake assembly comprises:

moving the brake chassis in a direction transverse to a longitudinal direction of the plurality of drive cables; and laterally aligning the one or more brakes with the one or more of the plurality of drive cables.

15. The method of claim 14, wherein actuating the cable brake assembly further comprises receiving an end of the brake chassis within a pocket defined in an inner sidewall of the cavity.

16. The method of claim 15, further comprising mating a key arranged at the end with the pocket and thereby preventing the brake chassis from rotating.

17. The method of claim 14, wherein laterally aligning the one or more brakes with the one or more of the plurality of drive cables comprises:

driving the one or more of the plurality of drive cables against an adjacent outer surface of the brake pad with the one or more brakes; and binding the one or more of the plurality of drive cables in place with the one or more brakes to prevent axial movement of the one or more of the plurality of drive cables.

18. The method of claim 13, further comprising locking the cable brake assembly in the second position with a locking assembly arranged at an end of the brake chassis.

19. The method of claim 13, wherein the cable brake assembly includes at least one support attached to a sidewall of the cavity and having the one or more brakes rotatably mounted thereto at an axle, and further includes a brake chassis including a leg that terminates with a key matable with a profile provided on the one or more brakes, and wherein actuating the cable brake assembly comprises:

moving the brake chassis in a direction transverse to a longitudinal direction of the plurality of drive cables;

mating the key with the profile and thereby preventing rotation of the one or more brakes on the axle; and binding the one or more of the plurality of drive cables in place with the one or more brakes to prevent axial movement of the one or more of the plurality of drive cables.

20. A cable brake assembly for a surgical tool operable with a plurality of drive cables, the cable brake assembly comprising:

a brake chassis;

one or more brakes engageable with one or more of the plurality of drive cables; and a brake pad engageable with one or more of the drive cables, wherein the brake chassis is movable between a first position, where the plurality of drive cables are free to move longitudinally within the elongate shaft, and a second position, where the one or more brakes and the brake pad engage and prevent the one or more of the plurality of drive cables from moving.

* * * * *